United States Patent
Winger

(10) Patent No.: US 9,513,253 B2
(45) Date of Patent: *Dec. 6, 2016

(54) DROPLET ACTUATORS AND TECHNIQUES FOR DROPLET-BASED ENZYMATIC ASSAYS

(75) Inventor: Theodore Winger, Morrisville, NC (US)

(73) Assignee: Advanced Liquid Logic, Inc., San Diego, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 14/131,846

(22) PCT Filed: Jul. 11, 2012

(86) PCT No.: PCT/US2012/046333
§ 371 (c)(1),
(2), (4) Date: Mar. 18, 2014

(87) PCT Pub. No.: WO2013/009927
PCT Pub. Date: Jan. 17, 2013

(65) Prior Publication Data
US 2014/0246319 A1 Sep. 4, 2014

Related U.S. Application Data

(60) Provisional application No. 61/506,369, filed on Jul. 11, 2011, provisional application No. 61/506,359, filed on Jul. 11, 2011.

(51) Int. Cl.
*G01N 27/447* (2006.01)
*B01L 3/00* (2006.01)

(52) U.S. Cl.
CPC ....... *G01N 27/447* (2013.01); *B01L 3/502792* (2013.01); *B01L 2300/0816* (2013.01); *B01L 2300/12* (2013.01); *B01L 2400/0424* (2013.01); *B01L 2400/0427* (2013.01); *G01N 2800/044* (2013.01)

(58) Field of Classification Search
None
See application file for complete search history.

(56) References Cited

U.S. PATENT DOCUMENTS

| | | | |
|---|---|---|---|
| 4,127,460 A | 11/1978 | Gaske et al. |
| 4,244,693 A | 1/1981 | Guon |
| 4,269,605 A | 5/1981 | Dean et al. |
| 4,390,403 A | 6/1983 | Batchelder |
| 4,636,785 A | 1/1987 | Le Pesant |
| 4,863,849 A | 9/1989 | Melamede |
| 4,911,782 A | 3/1990 | Brown |
| 5,038,852 A | 8/1991 | Johnson et al. |
| 5,176,203 A | 1/1993 | Larzul |
| 5,181,016 A | 1/1993 | Lee |
| 5,225,332 A | 7/1993 | Weaver et al. |
| 5,240,994 A | 8/1993 | Brink et al. |
| 5,266,498 A | 11/1993 | Tarcha et al. |
| 5,455,008 A | 10/1995 | Earley et al. |
| 5,472,881 A | 12/1995 | Beebe et al. |
| 5,486,337 A | 1/1996 | Ohkawa |
| 5,498,392 A | 3/1996 | Wilding et al. |
| 5,503,803 A | 4/1996 | Brown |
| 5,525,493 A | 6/1996 | Hornes et al. |
| 5,559,134 A | 9/1996 | Buchmann et al. |
| 5,720,923 A | 2/1998 | Haff et al. |
| 5,728,524 A | 3/1998 | Sibson |
| 5,753,186 A | 5/1998 | Hanley et al. |
| 5,770,391 A | 6/1998 | Foote et al. |
| 5,770,457 A | 6/1998 | Stocker et al. |
| 5,779,977 A | 7/1998 | Haff et al. |
| 5,817,526 A | 10/1998 | Kinoshita et al. |
| 5,827,480 A | 10/1998 | Haff et al. |
| 5,846,396 A | 12/1998 | Zanzucchi et al. |
| 5,851,769 A | 12/1998 | Gray et al. |
| 5,859,213 A | 1/1999 | Stefas et al. |
| 5,871,908 A | 2/1999 | Henco et al. |
| 5,945,281 A | 8/1999 | Prabhu et al. |
| 5,980,719 A | 11/1999 | Cherukuri et al. |
| 5,998,224 A | 12/1999 | Rohr et al. |
| 6,013,531 A | 1/2000 | Wang et al. |
| 6,033,880 A | 3/2000 | Haff et al. |
| 6,063,339 A | 5/2000 | Tisone et al. |
| 6,106,685 A | 8/2000 | McBride et al. |
| 6,130,098 A | 10/2000 | Handique et al. |
| 6,152,181 A | 11/2000 | Wapner et al. |
| 6,171,810 B1 | 1/2001 | Zhu |
| 6,180,372 B1 | 1/2001 | Franzen |

(Continued)

FOREIGN PATENT DOCUMENTS

| CN | 101472940 A | 7/2009 |
|---|---|---|
| DE | 10162188 A1 | 6/2003 |

(Continued)

OTHER PUBLICATIONS

Benton et al., "Library Preparation Method 1 DNA Library Construction for Illumine SBS Sequencing Platforms using NEBNext® Library Preparation Reagents", Application Note, NuGEN, 2011.
Boles et al., "Droplet-Based Pyrosequencing Using Digital Microfluidics", Analytical Chemistry, vol. 83, Sep. 2011, 8439-47.
Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.
Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-Dx-Wkshop/index.cfm, Jun. 28, 2011.

(Continued)

Primary Examiner — Ralph Gitomer
(74) Attorney, Agent, or Firm — Paul Liu; Illumina, Inc.

(57) ABSTRACT

Droplet actuators and techniques for droplet-based assays are provided. A method of conducting an assay comprises: incubating a droplet in oil, the droplet comprising an umbelliferone substrate, a sample potentially comprising an enzyme which cleaves the umbelliferone substrate, and a zwitterionic surfactant; and detecting a signal emitted from the droplet.

46 Claims, 8 Drawing Sheets

(56) References Cited

U.S. PATENT DOCUMENTS

| | | |
|---|---|---|
| 6,210,891 B1 | 4/2001 | Nyren et al. |
| 6,258,568 B1 | 7/2001 | Nyren |
| 6,294,063 B1 | 9/2001 | Becker et al. |
| 6,319,668 B1 | 11/2001 | Nova et al. |
| 6,379,929 B1 | 4/2002 | Burns et al. |
| 6,406,667 B1 | 6/2002 | Singh et al. |
| 6,432,290 B1 | 8/2002 | Harrison et al. |
| 6,453,928 B1 | 9/2002 | Kaplan et al. |
| 6,454,924 B2 | 9/2002 | Jedrzejewski et al. |
| 6,461,570 B2 | 10/2002 | Ishihara et al. |
| 6,473,492 B2 | 10/2002 | Prins et al. |
| 6,485,913 B1 | 11/2002 | Becker et al. |
| 6,538,823 B2 | 3/2003 | Kroupenkine et al. |
| 6,545,815 B2 | 4/2003 | Kroupenkine et al. |
| 6,548,308 B2 | 4/2003 | Ellson et al. |
| 6,548,311 B1 | 4/2003 | Knoll |
| 6,565,727 B1 | 5/2003 | Shenderov |
| 6,596,238 B1 | 7/2003 | Belder et al. |
| 6,613,560 B1 | 9/2003 | Tso et al. |
| 6,629,826 B2 | 10/2003 | Yoon et al. |
| 6,632,655 B1 | 10/2003 | Mehta et al. |
| 6,665,127 B2 | 12/2003 | Bao et al. |
| 6,673,533 B1 | 1/2004 | Wohlstadter et al. |
| 6,734,436 B2 | 5/2004 | Faris et al. |
| 6,761,962 B2 | 7/2004 | Bentsen et al. |
| 6,773,566 B2 | 8/2004 | Shenderov |
| 6,790,011 B1 | 9/2004 | Le Pesant et al. |
| 6,828,100 B1 | 12/2004 | Ronaghi |
| 6,841,128 B2 | 1/2005 | Kambara et al. |
| 6,846,638 B2 | 1/2005 | Shipwash |
| 6,896,855 B1 | 5/2005 | Kohler et al. |
| 6,911,132 B2 | 6/2005 | Pamula et al. |
| 6,924,792 B1 | 8/2005 | Jessop |
| 6,949,176 B2 | 9/2005 | Vacca et al. |
| 6,955,881 B2 | 10/2005 | Tanaami |
| 6,958,132 B2 | 10/2005 | Chiou et al. |
| 6,960,437 B2 | 11/2005 | Enzelberger et al. |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,078,168 B2 | 7/2006 | Sylvan |
| 7,108,354 B2 | 9/2006 | Gulvin et al. |
| 7,109,222 B2 | 9/2006 | Cheng et al. |
| 7,163,612 B2 | 1/2007 | Sterling et al. |
| 7,189,359 B2 | 3/2007 | Yuan et al. |
| 7,189,560 B2 | 3/2007 | Kim et al. |
| 7,211,223 B2 | 5/2007 | Fouillet et al. |
| 7,211,442 B2 | 5/2007 | Gilbert et al. |
| 7,251,392 B2 | 7/2007 | Kuiper et al. |
| 7,255,780 B2 | 8/2007 | Shenderov |
| 7,267,752 B2 | 9/2007 | King et al. |
| 7,310,080 B2 | 12/2007 | Jessop |
| 7,328,979 B2 | 2/2008 | Decre et al. |
| 7,329,545 B2 | 2/2008 | Pamula et al. |
| 7,338,760 B2 | 3/2008 | Gong et al. |
| 7,413,706 B2 | 8/2008 | Peeters et al. |
| 7,438,860 B2 | 10/2008 | Takagi et al. |
| 7,439,014 B2 | 10/2008 | Pamula et al. |
| 7,454,988 B2 | 11/2008 | Tan |
| 7,458,661 B2 | 12/2008 | Kim et al. |
| 7,459,311 B2 | 12/2008 | Nyren et al. |
| 7,495,031 B2 | 2/2009 | Sakuma et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,632,388 B2 | 12/2009 | Rikihisa et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 | 8/2010 | Adachi et al. |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,821,699 B1 | 10/2010 | Lo et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 * | 5/2011 | Smith ................. B01F 13/0071 204/600 |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 * | 1/2012 | Winger ................... C12Q 1/00 436/86 |
| 8,093,064 B2 | 1/2012 | Shah et al. |
| 8,137,917 B2 | 3/2012 | Pollack et al. |
| 8,147,668 B2 | 4/2012 | Pollack et al. |
| 8,179,216 B2 | 5/2012 | Knospe |
| 8,202,686 B2 * | 6/2012 | Pamula ............. B01L 3/502784 435/4 |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,292,798 B2 | 10/2012 | Califorrniaa |
| 8,304,253 B2 | 11/2012 | Yi et al. |
| 8,313,698 B2 | 11/2012 | Pollack et al. |
| 8,317,990 B2 | 11/2012 | Pamula et al. |
| 8,337,778 B2 | 12/2012 | Stone et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0001544 A1 | 1/2002 | Hess et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0093651 A1 | 7/2002 | Roe |
| 2002/0102595 A1 | 8/2002 | Davis |
| 2002/0102737 A1 | 8/2002 | Millington et al. |
| 2002/0125135 A1 | 9/2002 | Derand et al. |
| 2002/0128546 A1 | 9/2002 | Silver |
| 2002/0142483 A1 | 10/2002 | Yao et al. |
| 2002/0143437 A1 | 10/2002 | Handique et al. |
| 2002/0168671 A1 | 11/2002 | Burns et al. |
| 2002/0172969 A1 | 11/2002 | Burns et al. |
| 2003/0006140 A1 | 1/2003 | Vacca et al. |
| 2003/0007898 A1 | 1/2003 | Bohm et al. |
| 2003/0012483 A1 | 1/2003 | Ticknor et al. |
| 2003/0012699 A1 | 1/2003 | Moore et al. |
| 2003/0049177 A1 | 3/2003 | Smith et al. |
| 2003/0049632 A1 | 3/2003 | Edman et al. |
| 2003/0082081 A1 | 5/2003 | Fouillet et al. |
| 2003/0096221 A1 | 5/2003 | Littman et al. |
| 2003/0103021 A1 | 6/2003 | Young et al. |
| 2003/0119057 A1 | 6/2003 | Gascoyne et al. |
| 2003/0148538 A1 | 8/2003 | Ng |
| 2003/0164295 A1 | 9/2003 | Sterling |
| 2003/0170698 A1 | 9/2003 | Gascoyne et al. |
| 2003/0171325 A1 | 9/2003 | Gascoyne et al. |
| 2003/0183525 A1 | 10/2003 | Elrod et al. |
| 2003/0205632 A1 | 11/2003 | Kim et al. |
| 2003/0206351 A1 | 11/2003 | Kroupenkine |

(56) References Cited

U.S. PATENT DOCUMENTS

| | | |
|---|---|---|
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |
| 2004/0042721 A1 | 3/2004 | Kroupenkine et al. |
| 2004/0055536 A1 | 3/2004 | Kolar et al. |
| 2004/0055871 A1 | 3/2004 | Walton et al. |
| 2004/0055891 A1 | 3/2004 | Pamula et al. |
| 2004/0058450 A1 | 3/2004 | Pamula et al. |
| 2004/0086870 A1 | 5/2004 | Tyvoll et al. |
| 2004/0091392 A1 | 5/2004 | McBridge et al. |
| 2004/0101445 A1 | 5/2004 | Shvets et al. |
| 2004/0136876 A1 | 7/2004 | Fouillet et al. |
| 2004/0141884 A1 | 7/2004 | Unno et al. |
| 2004/0180346 A1 | 9/2004 | Anderson et al. |
| 2004/0185484 A1 | 9/2004 | Costa et al. |
| 2004/0209253 A1 | 10/2004 | Tam |
| 2004/0209376 A1 | 10/2004 | Natan et al. |
| 2004/0219557 A1 | 11/2004 | Dobrowolski et al. |
| 2004/0231987 A1 | 11/2004 | Sterling et al. |
| 2005/0031657 A1 | 2/2005 | Gilson et al. |
| 2005/0037507 A1 | 2/2005 | Gauer |
| 2005/0048581 A1 | 3/2005 | Chiu et al. |
| 2005/0056569 A1 | 3/2005 | Yuan et al. |
| 2005/0064423 A1 | 3/2005 | Higuchi et al. |
| 2005/0100675 A1 | 5/2005 | Mao et al. |
| 2005/0106742 A1 | 5/2005 | Wahl |
| 2005/0142037 A1 | 6/2005 | Reihs |
| 2005/0142563 A1 | 6/2005 | Haddad et al. |
| 2005/0148042 A1 | 7/2005 | Prestwich et al. |
| 2005/0158755 A1 | 7/2005 | Lee et al. |
| 2005/0158845 A1 | 7/2005 | Wikswo et al. |
| 2005/0179746 A1 | 8/2005 | Roux et al. |
| 2005/0189049 A1 | 9/2005 | Ohno et al. |
| 2005/0227264 A1 | 10/2005 | Nobile et al. |
| 2005/0227349 A1 | 10/2005 | Kim et al. |
| 2005/0282224 A1 | 12/2005 | Fouillet et al. |
| 2005/0287572 A1 | 12/2005 | Mathies et al. |
| 2006/0021875 A1 | 2/2006 | Griffith et al. |
| 2006/0039823 A1 | 2/2006 | Yamakawa et al. |
| 2006/0040375 A1 | 2/2006 | Arney et al. |
| 2006/0054503 A1 | 3/2006 | Pamula et al. |
| 2006/0068450 A1 | 3/2006 | Combette et al. |
| 2006/0078893 A1 | 4/2006 | Griffiths et al. |
| 2006/0102477 A1 | 5/2006 | Vann et al. |
| 2006/0132927 A1 | 6/2006 | Yoon |
| 2006/0164490 A1 | 7/2006 | Kim et al. |
| 2006/0166261 A1 | 7/2006 | Higuchi et al. |
| 2006/0166262 A1 | 7/2006 | Higuchi et al. |
| 2006/0172336 A1 | 8/2006 | Higuchi et al. |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2006/0254933 A1 | 11/2006 | Adachi et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0075922 A1 | 4/2007 | Jessop |
| 2007/0086927 A1 | 4/2007 | Natarajan et al. |
| 2007/0141593 A1 | 6/2007 | Lee et al. |
| 2007/0166810 A1 | 7/2007 | Bobrow et al. |
| 2007/0179641 A1 | 8/2007 | Lucas et al. |
| 2007/0202538 A1 | 8/2007 | Glezer et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0003588 A1 | 1/2008 | Hasson et al. |
| 2008/0006535 A1 | 1/2008 | Paik et al. |
| 2008/0018709 A1 | 1/2008 | Takenaka et al. |
| 2008/0023330 A1 | 1/2008 | Viovy |
| 2008/0038810 A1 | 2/2008 | Pollack et al. |
| 2008/0039636 A1 | 2/2008 | Harichian et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0089005 A1 | 4/2008 | Choi et al. |
| 2008/0105549 A1 | 5/2008 | Pamela et al. |
| 2008/0113081 A1 | 5/2008 | Hossainy et al. |
| 2008/0124252 A1 | 5/2008 | Marchand et al. |
| 2008/0138815 A1 | 6/2008 | Brown et al. |
| 2008/0142376 A1 | 6/2008 | Fouillet et al. |
| 2008/0151240 A1 | 6/2008 | Roth |
| 2008/0153091 A1 | 6/2008 | Brown et al. |
| 2008/0160525 A1 | 7/2008 | Brown et al. |
| 2008/0166793 A1 | 7/2008 | Beer et al. |
| 2008/0169184 A1 | 7/2008 | Brown et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171382 A1 | 7/2008 | Brown et al. |
| 2008/0206832 A1 | 8/2008 | Zheng et al. |
| 2008/0210558 A1 | 9/2008 | Sauter-Starace et al. |
| 2008/0213766 A1 | 9/2008 | Brown et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0053726 A1 | 2/2009 | Owen et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0166224 A1 | 7/2009 | Yang et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1* | 2/2010 | Pamula ............ B01L 3/502784 435/18 |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan |
| 2010/0236929 A1 | 9/2010 | Pollack et al. |

(56) References Cited

U.S. PATENT DOCUMENTS

| | | |
|---|---|---|
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0291578 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1* | 5/2011 | Winger ............ C12Q 1/00 506/7 |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0217113 A1 | 8/2013 | Srinivasan et al. |
| 2013/0217583 A1 | 8/2013 | Link et al. |
| 2013/0280131 A1 | 10/2013 | Handique et al. |

FOREIGN PATENT DOCUMENTS

| | | |
|---|---|---|
| EP | 0221561 A2 | 5/1987 |
| EP | 1510254 A2 | 3/2003 |
| EP | 1418243 A1 | 5/2004 |
| JP | 5025159 A | 2/1993 |
| JP | 2006078225 A | 3/2006 |
| JP | 2006317364 A | 11/2006 |
| JP | 2006329899 A | 12/2006 |
| JP | 2006329904 A | 12/2006 |
| JP | 2008096590 A | 4/2008 |
| WO | 9111172 A1 | 8/1991 |
| WO | 9822625 A1 | 5/1998 |
| WO | 9915876 A1 | 4/1999 |
| WO | 9917093 A1 | 4/1999 |
| WO | 9954730 A1 | 10/1999 |
| WO | 0069565 A1 | 11/2000 |
| WO | 0073655 A1 | 12/2000 |
| WO | 0207503 A1 | 1/2002 |
| WO | 0218539 A2 | 3/2002 |
| WO | 0345556 A1 | 6/2003 |
| WO | 03069380 A1 | 8/2003 |
| WO | 2004011938 A2 | 2/2004 |
| WO | 2004027490 A1 | 4/2004 |
| WO | 2004029585 A1 | 4/2004 |
| WO | 2004030820 | 4/2004 |
| WO | 2004073863 A2 | 9/2004 |
| WO | 2005047696 A1 | 5/2005 |
| WO | 2005069015 A1 | 7/2005 |
| WO | 2006003292 A1 | 1/2006 |
| WO | 2006013303 A1 | 2/2006 |
| WO | 2006026351 A1 | 3/2006 |
| WO | 2006070162 A1 | 7/2006 |
| WO | 2006081558 | 8/2006 |
| WO | 2006085905 A1 | 8/2006 |
| WO | 2006124458 A2 | 11/2006 |
| WO | 2006127451 A2 | 11/2006 |
| WO | 2006129486 A1 | 12/2006 |
| WO | 2006132211 A1 | 12/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007094739 | 8/2007 |
| WO | 2007120240 A2 | 10/2007 |
| WO | 2007120241 A2 | 10/2007 |
| WO | 2007123908 A2 | 11/2007 |
| WO | 2007133710 A1 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032167 A1 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 A1 | 4/2009 |
| WO | 2009052348 A2 | 4/2009 |
| WO | 2009076414 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010004014 A1 | 1/2010 |
| WO | 2010006166 A2 | 1/2010 |
| WO | 2010009463 A2 | 1/2010 |
| WO | 2010019782 A2 | 2/2010 |
| WO | 2010027894 A2 | 3/2010 |
| WO | 2010042637 A2 | 4/2010 |
| WO | 2010077859 A3 | 7/2010 |
| WO | 2010106222 A2 | 9/2010 |
| WO | 2011002957 A2 | 1/2011 |
| WO | 2011020011 A2 | 2/2011 |
| WO | 2011057197 A2 | 5/2011 |
| WO | 2011084703 A2 | 7/2011 |
| WO | 2011126892 A2 | 10/2011 |
| WO | 2012009320 A2 | 1/2012 |
| WO | 2012012090 A2 | 1/2012 |
| WO | 2012037308 A2 | 3/2012 |
| WO | 2012068055 A3 | 5/2012 |
| WO | 2013009927 A3 | 1/2013 |
| WO | 2013169722 A1 | 11/2013 |

OTHER PUBLICATIONS

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International

(56) References Cited

OTHER PUBLICATIONS

Conference on Computer Design, San Jose, CA, Oct. 1-4, 2006, 93-100.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems, 1(3), Oct. 2005, 186-223.
Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Lead", Sensors and Actuators, vol. 73, Issues 1-2, Mar. 1999, pp. 30-36.
Cohen, "Automated Multianalyte Screening Tool for Classification of Forensic Samples", NIJ conference 2012, http://www.nij.gov/nij/events/nij_conference/2012/nij-2012-program-book.pdf, 2012.
Cohen, "Digital Microfluidic Sample Prep & Bioanalytical Systems", BioDot Workshop: From R&D to Quantitative IVDs, Irvine, CA, Apr. 24, 2012.
Cotten et al., "Digital Microfluidics: a novel platform for multiplexed detection of lysosomal storage diseases", Abstract # 3747.9. Pediatric Academic Society Conference, 2008.
DeLapierre et al., "SmartDrop: An Integrated System from Sample Collection to Result using real-time PCR," 4th National Bio-Threat Conference, Dec. 7-9, 2010, New Orleans, LA, USA; Abstract in Proceedings, Poster presented at conference.
DeLattre, Movie in news on TF1 (at 12'45" Cyril Delattre), http://videos.tf1.fr/jt-we/zoom-sur-grenoble-6071525.html, 2009.
DeLattre, Movie in talk show "C Dans l'air" (at 24" Cyril Delattre), http://www.france5.fr/c-dans-l-air/sante/bientot-vous-ne-serez-plus-malade-31721, 2009.
DeLattre, Movie on Web TV—Cite des sciences (at 3'26" Cyril Delattre), http://www.universcience.tv/video-laboratoire-de-poche-793.html, 2009.
DeLattre et al., "Macro to microfluidics system for biological environmental monitoring", Biosensors and Bioelectronics, vol. 36, Issue 1, 2012, Available online, Apr. 27, 2012, 230-235.
DeLattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.
DeLattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.
DeLattre et al., "Towards an industrial fabrication process for electrowetting chip using standard MEMS Technology", µTAS2008, San Diego; poster presented, Oct. 15, 2008.
DeLattre et al., "Towards an industrial fabrication process for electrowetting chip using standard MEMS Technology", µTAS2008, San Diego; Abstract in proceedings, Oct. 13-16, 2008, 1696-1698.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Eckhardt et al., "Development and validation of a single-step fluorometric assay for Hunter syndrome", APHL Newborn Screening and Genetic Testing Symposium, San Diego, 2011.

Emani et al., "Novel microfluidic platform for automated lab-on-chip testing of hypercoagulability panel", Blood Coagulation and Fibrinolysis, vol. 23(8), 2012, 760-8.
Emani et al., "Novel Microfluidic Platform for Point of Care Hypercoagulability Panel Testing", Circulation, vol. 122, 2010, A14693.
Fair et al., "A Micro- Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Workshop, Rochester, NY, May 31, 2006.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fair, "Scaling of Digital Microfluidic Devices for Picoliter Applications", The 6th International Electrowetting Meeting, Aug. 20-22, 2008, p. 14.
Fouillet, "Bio-Protocol Integration in Digital Microfluidic Chips", The 6th International Electrowetting Meeting, Aug. 20-22, 2008, p. 15.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Fouillet et al., "Digital microfluidic design and optimization of classic and new fluidic functions for lab on a chip systems", Microfluid Nanofluid, vol. 4, 2008, 159-165.
Graham et al., "Development of Quality Control Spots for Lysosomal Storage Disorders under cGMP", APHL Newborn Screening and Genetic Testing Symposium, San Diego, 2011.
Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.
Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008.
Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.
Jary et al., "SmartDrop, Microfluidics for Biology", Forum 4i 2009, Grenoble, France; Flyer distributed at booth, May 14, 2009.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.

(56) References Cited

OTHER PUBLICATIONS

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99-3800, 30th AIAA Fluid Dynamics Conference, Norfolk, VA, (Invited lecture), Jun. 1999, pp. 1-6.

Kleinert et al., "Dynamics and Stability of Oil Films During Droplet Transport by Electrowetting", 86th ACS Colloid & Surface Science Symposium, Abstract, Jun. 13, 2012.

Kleinert et al., "Dynamics and Stability of Oil Films During Droplet Transport by Electrowetting", 86th ACS Colloid & Surface Science Symposium, Presentation, Jun. 13, 2012.

Kleinert et al., "Dynamics and stability of oil films during droplet transport by electrowetting", 8th International Meeting on Electrowetting, Athens, Greece, Jun. 21-23, 2012.

Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008. org., Jun. 15-18, 2008.

Kleinert, "Electric-Field-Assisted Convective Assembly of Colloidal Crystal Coatings", Langmuir, vol. 26(12), May 13, 2010, 10380-10385.

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.

Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010054501000239000000, Aug. 1-5, 2010.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Applications of tandem mass spectrometry and microfluidics in newborn screening", Southeastern Regional Meeting of the American Chemical Society, Raleigh, North Carolina, 2012.

Millington et al., "Digital microfluidics: a future technology in the newborn screening laboratory", Seminars in Perinatology, vol. 34, Apr. 2010, 163-169.

Millington et al., "Digital Microfluidics: a novel platform for multiplexed detection of LSDs with potential for newborn screening", Association of Public Health Laboratories Annual Conference, San Antonio, TX, Nov. 4, 2008.

Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; POSTER, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik et al., "Programmable flow-through real-time PCR using digital microfluidics", Proc. Micro Total Analysis Systems (µTAS), Handout, 2007.

Paik et al., "Programmable flow-through real-time PCR using digital microfluidics", Proc. Micro Total Analysis Systems (µTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "A droplet-based lab-on-a-chip for colorimetric detection of nitroaromatic explosives", Proceedings of Micro Electro Mechanical Systems, 2005, 722-725.

Pamula et al., "Cooling of integrated circuits using droplet-based microfluidics", Proc. ACM Great Lakes Symposium on VLSI, Apr. 2003, 84-87.

Pamula, "Digital microfluidic lab-on-a-chip for multiplexing tests in newborn screening", Newborn Screening Summit: Envisioning a Future for Newborn Screening, Bethesda, MD, Dec. 7, 2009.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.

Pamula et al., "Digital Microfluidic Platform for Multiplexing LSD Assays in Newborn Screening", LSD World Meeting, Las Vegas, NV, Feb. 16-18, 2011.

Pamula et al., "Digital Microfluidics Platform for Lab-on-a-chip applications", Duke University Annual Post Doctoral Research Day, 2002.

(56) References Cited

OTHER PUBLICATIONS

Pamula et al., "Microfluidic electrowetting-based droplet mixing", IEEE, 2002, 8-10.
Pamula et al., "Rapid LSD assays on a multiplex digital microfluidic platform for newborn screening", Lysosomal Disease Network World Symposium 2012, San Diego, CA, Feb. 8-19, 2012, 39.
Pamula, "Sample Preparation and Processing using Magnetic Beads on a Digital Microfluidic Platform", CHI's Genomic Sample Prep, San Francisco, CA, Jun. 9-10, 2009.
Pamula, "Sample-to-sequence-molecular diagnostics on a digital microfluidic lab on a chip", Pre-conference workshops, 4th International Conference on Birth Defects and Disabilities in the Developing World, New Delhi, India, Oct. 4, 2009.
Pollack et al., "Applications of Electrowetting-Based Digital Microfluidics in Clinical Diagnostics", Expert Rev. Mol. Diagn., vol. 11(4), 2011, 393-407.
Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Pollack, "Sample Preparation Using Digital Microfluidics", Sample Prep 2012, Knowledge Press, Inc., May 3-4, 2012.
Punnamaraju, "Voltage and Photo Induced Effects in Droplet-Interface-Bilayer Lipid", PhD Thesis, University of Cincinnati, 2011.
Punnamaraju et al., "Voltage Control of Droplet Interface Bilayer Lipid Membrane Dimensions", Langmuir the ACS Journal of Surfaces and Colloids, vol. 27, Issue 2, 2011, Published on Web, Dec. 10, 2010, 618-626.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting- based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.

Rival et al., "Expression de gènes de quelques cellules sur puce EWOD/Gene expression of few cells on EWOD chip", iRTSV,http://www-dsy.cea.fr/var/plain/storage/original/media/File/iRTSV/thema_08(2).pdf (english translation), Winter 2009-2010.
Rival et al., "New insight on droplet dynamics under electrowetting actuation and design tools for speeding up product development", 8th Electrowetting Workshop, Athens, Greece. Abstract, 2012.
Rival et al., "New insight on droplet dynamics under electrowetting actuation and design tools for speeding up product development", 8th Electrowetting Workshop, Athens, Greece, Presentation, 2012.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.
Rival et al., "Towards single cells gene expression preparation and analysis on ewod lab on chip", Lab on Chip Europe 2009, Abstract in proceedings, May 19-20, 2009.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Schell et al., "Evaluation of a Digital Microfluidic real-time PCR Platform to detect DNA of Candida albicans", Eur. J. Clin Microbiol Infect Dis, Published on-line DOI 10.1007/s10096-012-15616, Feb. 2012.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Shi et al., "Evaluation of stability of fluorometric reagent kits for screening of Lysosomal Storage Disorders", APHL Newborn Screening and Genetic Testing Symposium, San Diego, 2011.
Sista et al., "96-Immunoassay Digital Microfluidic Multiwell Plate", Proc. µTAS, Oct. 12-16, 2008.
Sista, "Development of a Digital Microfluidic Lab-on-a-Chip for Automated Immunoassays with Magnetically Responsive Beads", PhD Thesis, Department of Chemical Engineering, Florida State University, 2007.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Digital Microfluidic Platform for Multiplexing Enzyme Assays: Implications for Lysosomal Storage Disease Screening in Newborns", Clinical Chemistry, vol. 57, Aug. 22, 2011, 1444-51.
Sista et al., "Digital Microfluidic platform for multiplexing LSD assays in newborn screening", APHL Newborn Screening and Genetic Testing Symposium, Orlando, May 3-6, 2010.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Multiplex Digital Microfluidic Platform for Rapid Newborn Screening of Lysosomal Storage Disorders", ACMG Annual Meeting, Charlotte, NC, 2012.
Sista et al., "Performance of a digital microfluidic assay for Gaucher and Hurler disorders", APHL Newborn Screening and Genetic Testing Symposium, San Diego, 2011.

(56) References Cited

OTHER PUBLICATIONS

Sista et al., "Rapid, Single-Step Assay for Hunter Syndrome in Dried Blood Spots Using Digital Microfluidics", Clinica Chimica Acta, vol. 412, 2011, 1895-97.
Sista et al., "Spatial multiplexing of immunoassays for small-vol. samples", 10th PI Meeting IMAT, Bethesda, 2009.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Digital Microfluidic Lab-on-a-Chip for Protein Crystallization", The 82nd ACS Colloid and Surface Science Symposium, 2008.
Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.
Srinivasan et al., "Feasibility of a point of care newborn screening platform for hyperbirilirubinemia", APHL Newborn Screening and Genetic Testing Symposium, San Diego, 2011.
Srinivasan et al., "Low cost digital microfluidic platform for protein crystallization", Enabling Technologies for Structural Biology, NIGMS Workshop, Bethesda, MD., Mar. 4-6, 2009, J-23.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 7275.
Su et al., "Yield Enhancement of Digital Microfluidics-Based Biochips Using Space Redundancy and Local Reconfiguration", Proc. Design, Automation and Test in Europe (Date) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, May 2004, 3229-3235.
Thwar et al., "DNA sequencing using digital microfluidics", Poster 42, 41st AACC's Annual Oak Ridge Conference Abstracts, Clinical Chemistry vol. 55, 2009, 1891.
Tolun et al., "A Novel Fluorometric Enzyme Analysis Method for Hunter Syndrome Using Dried Blood Spots", Mol. Genet. Metab., 105, Issue 3, 2012; doi:10.1016/j.ymgme.2011.12.011, Epub, Dec. 21, 2011 519-521.
Tolun et al., "Dried blood spot based enzyme assays for lysosomal storage disorders", 2011 Tokyo Meeting on Lysosomal Storage Disease Screening, Tokyo, Aug. 5, 2011.
Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Weaver, "Application of Magnetic Microspheres for Pyrosequencing on a Digital Microfluidic Platform", Department of Electrical and Computer Engineering, Duke University, 2005.
Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.
Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu et al., "Automated solution preparation on a digital microfluidic lab-on-chip", PSI Bottlenecks Workshop, 2008.
Xu et al., "Automated, Accurate and Inexpensive Solution-Preparation on a Digital Microfluidic Biochip", Proc. IEEE Biomedical Circuits and Systems Conference (BioCAS), 2008, 301-304.
Xu et al., "Defect-Aware Synthesis of Droplet-Based Microfluidic Biochips", IEEE, 20th International Conference on VLSI Design, 2007.
Xu et al., "Defect-Tolerant Design and Optimization of a Digital Microfluidic Biochip for Protein Crystallization", IEEE Transactions on Computer Aided Design, vol. 29, No. 4, 2010, 552-565.
Xu et al., "Design and Optimization of a Digital Microfluidic Biochip for Protein Crystallization", Proc. IEEE/ACM International Conference on Computer-Aided Design (ICCAD), Nov. 2008, 297-301.
Xu et al., "Digital Microfluidic Biochip Design for Protein Crystallization", IEEE-NIH Life Science Systems and Applications Workshop, LISA, Bethesda, MD, Nov. 8-9, 2007, 140-143.
Xu et al., "Droplet-Trace-Based Array Partitioning and a Pin Assignment Algorithm for the Automated Design of Digital Microfluidic Biochips", CODES, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yang et al., "Manipulation of droplets in microfluidic systems", Trends in Analytical Chemistry, vol. 29, Feb. 2010, 141-157.
Yao et al., "Spot Cooling Using Thermoelectric Microcooler", Proc. 18th Int. Thermoelectric Conf, Baltimore, VA, pp. 256-259, Aug. 1999.
Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation on addressable single-side coplanar electrodes", Journal of Micromechanics and Microengineering, vol. 16.,Oct. 2006, 2053-2059.
Yi et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

(56) References Cited

OTHER PUBLICATIONS

Yi, "Soft Printing of Biological Liquids for Micro-arrays: Concept, Principle, Fabrication, and Demonstration", Ph.D. dissertation, UCLA, 2004.
Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.
Yi et al., "Soft Printing of Droplets Pre-Metered by Electrowetting", Sensors and Actuators A: Physical, vol. 114, Jan. 2004, 347-354.
Zeng et al., "Actuation and Control of Droplets by Using Electrowetting-on-Dielectric", Chin. Phys. Lett., vol. 21(9), 2004, 1851-1854.
Zhao et al., "Droplet Manipulation and Microparticle Sampling on Perforated Microfilter Membranes", J. Micromech. Microeng., vol. 18, 2008, 1-11.
Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.
Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.
Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.
Zhao et al., "Optimization Techniques for the Synchronization of Concurrent Fluidic Operations in Pin-Constrained Digital Microfluidic Biochips", IEEE Transactions on Very Large Scale Integration (VLSI) Systems, vol. 20, No. 6, Jun. 2012, 1132-1145.
Zhao et al., "Synchronization of Concurrently-Implemented Fluidic Operations in Pin-Constrained Digital Microfluidic Biochips", VLSI Design, (Best Paper Award), 2010.
International Search Report dated Jan. 30, 2013 from PCT International Application No. PCT/US2012/046333.
PCT International Preliminary Report on Patentability for PCT/US2012/046333 dated Jan. 14, 2014.
Abstract from National Institutes of Health Grant No. 1R01HG004354-01 titled "Continuous Sequencing-By-Synthesis Based on a Digital Microfluidic Platform" with a project start date of Aug. 1, 2007.
Binks, "Wetting: theory and experiment", Current Opinion in Colloids and Interface Science, vol. 6, No. 1, 17-21, 2001.
Chamberlain, et al., "Deletion screening of Duchenne musular dystrophy locus via multiplex DNA amplification", Nuc. Acid. Res. 16, pp. 11141-11156, 1988.
Cho, et al., "Concentration and binary separation of micro particles for droplet-based digital microfluidics", Lab Chip, vol. 7, 490-498, 2007.
Coltro et al., "Toner and paper-based fabrication techniques for microfluidic applications", Electrophoresis, vol. 31, 2487-2498, Jul. 2010.
Delattre, Movie in news on TF1 (at 12'37" Cyril Delattre), http://videos.tf1.fr/it-we/zoom-sur-grenoble-6071525.html, 2009, (English translation of audio).
Delattre, Movie in talk show "C Dans l'air" (at 24"Cyril Delattre), http://www.france5.fr/c-dans-l-air/sante/bientot-vous-ne-seraz-plus-malade-31721, 2009, (English translation of audio).
Delattre, Movie on Web TV—Cite des sciences (at 3'26" Cyril Delattre), http://www.universcience.tv/video-laboratoire-de-poche-793.html, 2009, (English translation of audio).
Dorfman, et al., "Contamination-Free Continuouse Flow Microfluidic Polymerase Chain Reaction for Quantitative and Clinical Applications", Analytical Chemistry 77, 3700-3704, 2005.
Fowler, "Labon-on-a-Chip Technology May Present New ESD Challenges", Electrostatic Discharge (ESD) Journal. Retrieved on Apr. 18, 2008 from:http://www.esdjournal.com/articles/labchip/Lab.htm., Mar. 2002

Gijs, Mam, "Magnetic bead handling on-chip:new opportunities for analytical applications", Microfluidics and Nanofluidics, vol. 1, 22-40, Oct. 2, 2004.
Huang, et al., "MEMS-based sample preparation for molecular diagnostics", Analytical and Bioanalytical Chemistry, vol. 372, 49-65, 2002.
Jones, et al., "Dielectrophoretic liquid actuation and nanodroplet formation", J. Appl. Phys., vol. 89, No. 2, 1441-1448, Jan. 2001.
Kim, et al., "Electrowetting on paper for electronic paper display", ACS Applied Materials & Interfaces, vol. 2, 3318-3323, Nov. 2010.
Margulies, et al., "Genome sequencing in microfabricated high-density picolitre reactors", Nature, vol. 437, 376-380 and Supplemental Materials, 2005.
Pamula et al., "Digital Microfluidics for Lab-on-a-Chip Applications", "Emerging CAD Challenges for Biochip Design" Workshop, Conference on Design, Automation, and Test in Europe (DATE), Munich, Germany, Advance Programme, pp. 85-87, 2006.
Park, et al., "Single-sided continuous optoelectrowetting (SCOEW) droplet manipulation with light patterns", Lab on a chip, vol. 10, 1655-1661, Jul. 2010.
Pinho, et al., "Haemopoietic progenitors in the adult mouse omentum: permanent production of B lymphocytes and monocytes", Cell Tissue Res., vol. 319, No. 1, 91-102, Jan. 2005.
Poliski, Making materials fit the future: accommodating relentless technological requirements means researchers must recreate and reconfigure materials, frequently challenging established laws of physics, while keeping an eye on Moore's Law, R&D Magazine Conference, Dec. 2001
Raj, et al., Composite Dielectrics and Surfactants for Low Voltage Electrowetting Devices, University/Government/Industry Micro/Nano Symposium, vol. 17, 187-190, Jul. 13-16, 2008.
Russom, et al., "Pyrosequencing in a Microfluidic Flow-Through Device", Anal. Chem. vol. 77, 7505-7511, 2005.
Schwartz, et al., "Dielectrophoretic approaches to sample preparation and analysis", The University of Texas, Dissertation, Dec. 2001.
Shah, et al., "EWOD-driven droplet microfluidic device integrated with optoelectronic tweezers as an automated platform for cellular isolation and analysis", Lab on a Chip, vol. 9, 1732-1739, Jun. 2009.
Tsuchiya, et al., "On-chip polymerase chain reaction microdevice employing a magnetic droplet-manipulation system", Sensors and Actuators B, vol. 130, 583-588, Oct. 18, 2007.
Welch, et al., "Picoliter DNA sequencing chemistry on an electrowetting-based digital microfluidic platform", Biotechnology Journal, vol. 6, 165-176, Feb. 2011.
Wheeler, et al., "Electrowetting-Based Microfluidics for Analysis of Peptides and Proteins by Matrix-Assisted Laser Desportion/Ionization Mass Spectrometry", Anal. Chem. 76, 4833-4838, 2004.
Yi et al., "Microfluidics technology for manipulation and analysis of biological cells", Analytica Chimica Acta, vol. 560, 1-23, 2006.
Office Action dated Jul. 13, 2015 from U.S. Appl. No. 14/520,736.
Office Action dated Jan. 25, 2016 from U.S. Appl. No. 14/520,736.
Yonezawa et al. "DNA display for in vitro selection of diverse peptide libraries" Nucleic Acid Research, Oct. 1, 2003, vol. 31, No. 19.
Zheng et al. "Selection of restriction endonucleases using artificial cells" Nucleic Acid Research Jun. 12, 2007, vol. 35, No. 11.
International Search Report dated Jan. 6, 2012 from PCT International Application No. PCT/US2011/025711.
International Preliminary Report on Patentability dated Aug. 28, 2012 from PCT International Application No. PCT/US2011/025711.
Office Action dated Jan. 27, 2014 from related U.S. Appl. No. 13/596,965.
Office Action dated Jul. 22, 2014 from related U.S. Appl. No. 13/596,965.
Office Action dated Jan. 22, 2014 from related U.S. Appl. No. 13/581,354.
Office Action dated Jul. 21, 2014 from related U.S. Appl. No. 13/581,354.
Head et al., "Library construction for next-generation sequencing: Overviews and challenges", Biotechniques, Author Manuscript, Mar. 6, 2015, 56(2): 61-passim. doi:10.2144/000114133.

(56) References Cited

OTHER PUBLICATIONS

Caruccio et al. Nature Methods 16.3; Oct. 2009.
Srinivasan et al., "Commercializing electrowetting-based digital microfluidics: from the lab to a product", 8th International Meeting on Electrowetting, Athens, Greece, Jun. 21-23, 2012.
Office Action dated Dec. 27, 2013 from related U.S. Appl. No. 13/390,121.
Office Action dated Jun. 24, 2014 from related U.S. Appl. No. 13/390,121.
Mao et al (BMC Biotechnology, 7:76, Nov. 1-16, 2007).
Office Action dated Jul. 20, 2011 from related U.S. Appl. No. 13/012,831.
Murphey et al., "Screening tests for argininosuccinic aciduria, orotic aciduria, and other inherited enzyme deficiencies using dried blood specimens", Biochemical Genetics, vol. 6, No. 1, pp. 511-591, DOI: 10.1007/ BF00485965(1972).
Terry et al. A Gas Chromatographic Air Analyzer Fabricated on a Silicon Wafer, IEEE Transactions on Electron Devices, vol. ED-26, 1979, pp. 1880-1886.
Tuckerman and Pease, "High-Performance Heat Sinking for VLSI,"IEEE Electron Device Letters, 1981, pp. 126-129.
Batchelder "Dielectrophoretic manipulator," Review of Scientific Instruments, vol. 54, 1983, pp. 300-302.
Manz et al. "Miniaturized Total Chemical Analysis Systems: a Novel Concept for Chemical Sensing," Sensors and Actuators B: Chemical, 1990, pp. 244-248.
Welters et al. "Fast Electrically Switchable Capillary Effects," Langmuir, vol. 14, Mar. 1998, pp. 1535-1538.
McDonald et al. "Fabrication of Microfluidic systems in poly (dimethylsiloxane)," Electrophoresis, vol. 21, 2000, pp. 27-40.
Wego et al. "Fluidic microsystems based on printed circuit board technology," Journal of Micromechanics and Microengineering, vol. 11, No. 5, pp. 528-531 (Sep. 2001).
Moon et al., "Low voltage electrowetting-on-dielectric," Journal of Applied Physics, vol. 92 (7): pp. 4080-4087, Oct 1, 2002.
Locascio et al. "Polymer microfluidic devices," Talanta, vol. 56, Feb. 2002, pp. 267-287.
Garrell et al., "Preventing Biomolecular Adsorption in Electrowetting-Based Biofluidic Chips," Analytical Chemistry, vol. 75, Oct. 2003, pp. 5097-5102.
Chiou et al. "Light actuation of liquid by optoelectrowetting," Sensors and Actuators A: Physical, vol. 104, May 2003, pp. 222-228.
Squires and Quake, "Microfluidics: Fluid physics at the nanoliter scale," Reviews of Modern Physics, vol. 77, Oct. 2005, pp. 977-1-26.
Guttenberg et al., "Planar chip devices for PCR and hybridization with surface acoustic wave pump.," Lab on a chip, vol. 5, Mar. 2005, pp. 12617-12622.
Yager et al. "Microfluidic diagnostic technologies for global public health," Nature, vol. 442, 2006, pp. 412-418.
Cooney et al. Microfluidics and Nanofluidics, vol. 2 Mar. 2006, pp. 435-446.
Chatterjee et al. "Droplet-based microfluidics with nonaqueous solvents and solutions.," Lab on a Chip, vol. 6, Feb. 2006, pp. 199-206.
Madou et al. "Lab on a CD," Annual Review of Biomedical Engineering, vol. 8, pp. 601-628, 2006.
Yi and Kim, "Characterization of electrowetting actuation on addressable single-side coplanar electrodes," Journal of Micromechanics and Microengineering, vol. 16, Oct. 2006, pp. 2053-2059.
Dubois et al. "Ionic Liquid Droplet as e-Microreactor," Analytical Chemistry, vol. 78, 2006, pp. 4909-4917.
Whitesides, G.M., "The origins and the future of microfluidics," Nature, vol. 442, 2006, pp. 368.
Chin et al. "Lab-on-a-chip devices for global health: past studies and future opportunities.," Lab on a Chip, vol. 7, Jan. 2007, pp. 41-57.

Baviere et al. Dynamics of droplet transport induced by electrowetting actuation, Microfluidics and Nanofluidics, vol. 4, May 2007, pp. 287-294.
The et al. Droplet microfluidics., Lab on a chip, vol. 8 Feb. 2008, pp. 198-220.
Barbulovic-Nad et al. "Digital microfluidics for cell-based assays.," Lab on a chip, vol. 8, Apr. 2008, pp. 519-526.
Huebner et al. "Microdroplets: a sea of applications?," Lab on a Chip, vol. 8, Aug. 2008, pp. 1244-1254.
Gong and Kim,"Direct-referencing two-dimensional-array digital microfluidics using multi-layer printed circuit board," Journal of Microelectromechanical Systems, vol. 17, Jan. 2008, pp. 257-264.
Miller and Wheeler, "A Digital Microfluidic Approach to Homogeneous Enzyme Assays," Analytical Chemistry, vol. 80, 2008, pp. 1614-1619.
Luk Pluronic additives: a solution to sticky problems in digital microfluidics.,: Langmuir: The ACS journal of surfaces ans colloids, vol. 24, Jun. 2008, pp. 6382-6389.
Mariella, "Sample preparation: the weak link in microfluidics-based biodelection.,"Biomedical Microdevices, vol. 10, Dec. 2008, pp. 777-784.
Brassard "Water-oil core-shell droplets for electrowetting-based digital microfluidic devices.," Lab on a chip, vol. 8, Aug. 2008, pp. 1342-1349.
Mukhopadhyay, "Microfluidics: on the slope of enlightenment." Analytical chemsitry vol. 81, Jun. 2009, pp. 4169-4173.
Mousa "Droplet—scale estrogen assays in breast tissue, blood, and serum.," Science Translational Medicine, vol. 1 Oct. 2009; p. Ira2.
Poulos et al. "Electrowetting on dielectric-based microfluidics for integrated lipid bilayer formation and measurement," Applied Physics Letters, vol. 95, 2009, p. 013706.
Langelier et al. "Acoustically driven programmable liquid motion using resonance cavities" Proceedings of the National Academy of Sciences of the USA, vol. 106, Aug. 2009, pp. 12617-12622.
Malic et al. "Biochip functionalization using electrowetting-on-dielectric digital microfluidics for surface plasmon resonance imaging detection of DNA hybridization.," Biosensors & Bioelectronics, vol. 24, Mar. 2009, pp. 2218-2224.
Haeberle et al. "Microfluidic lab-on-a chip platforms: requirements, characteristics and applications," Chemical Society reviews, vol. 39, Mar. 2010, pp. 1153-1182.
Jebrail and Wheeler "Lets get digital: digitizing chemical biology with microfluidics.," Current Opinion in Chemical Biology, vol. 14, Oct. 2010, pp. 574-581.
Malic et al. "Integration and detection of biochemical assays in digital microfluidic LOC devices," Lab on a chip, vol. 10, Feb. 2010, pp. 418-431.
Shin and Lee "Machine vision for digital microfluidics," Review of Scientific Instruments, vol. 81, 2010,48 p. 014302.
Becker, "Mind the gap!," Lab on a chip, vol. 10, Feb. 2010, pp. 271-273.
Ding, "System level architectural optimization of semi-reconfigurable microfluidic system," M.S. Thesis, Duke University Dept of Electrical Engineering, 2000.
Moon "Electrowetting-on-dielectric microfluidics: Modeling, physics, and MALDI application," University of California, Los Angeles, 2006.
Hoshiyama et al., "Complexation and proton dissociation behavior of 7-hydroxy-4-methylcoumarin and related compounds in the presence of β-cyclodextrin", Journal of Photochemistry and Photobiology A: Chemistry 138 (2001 ), pp. 227-233.
Wiederschain et al. "Characterization of6-hexadecanoylamino-4-methylumbelliferyl-JI-D-galactopyranoside as ftuorogenic substrate of galactocerebrosidase for the diagnosis of Krabbe disease", (1992) Clinica Chimica Acta, 205 (1-2), pp. 87-96.
Svennerholm et al., Clinica Chimica Acta, vol. 106, Issue 2, Sep. 25, 1980, pp. 183-193; "Assay of the II-glucosidase activity with natural labelled and artificial substrates in leukocytes from homozygotes and heterozygotes with the norrbollnian type (type 3) of Gaucher disease".
Broadhead et al., Clinica Chemica Acta, vol. 75, Issue 1, Feb. 15, 1977, pp. 155-161, "The diagnosis of gaucher's disease in liver using 4-methylumbelliferyl-JL-d-glucopyranoside".

(56) References Cited

OTHER PUBLICATIONS

Besley and Moss "Studies on sphingomyelinase and JI-glucosidase activities in Niemann-Pick disease variants. Phosphodiesterase activities measured with natural and artificial substrates", (1983) Biochimica et Biophysica Acta—Lipids and Lipid Metabolism, 752 (1), pp. 54-64.

Boggs "Detection of Inborn Errors of Metabolism", Critical Reviews in Clinical Laboratory Sciences 1971, vol. 2, No. 4 : pp. 529-572.

Hopwood et al., "A fluorometric assay using 4-methylumbelliferyl alpha-L-iduronide for the estimation of alpha-L- iduronidase activity and the detection of Hurler and Scheie syndromes," Clin Chim Acta. 92(2): pp. 257-265, 1979.

Office Action dated Mar. 29, 2011 from related U.S. Appl. No. 12/789,891.

Office Action dated Sep. 21, 2011 from related U.S. Appl. No. 12/789,891.

Noderer (DNA pyrosequencing using microfluidic chips, NNIN REU Research Accomplishments, 2005, pp. 96-97).

Schwartz et al. "Droplet-based chemistry on a programmable micro-chip", Lab on a Chip, 2004, 4(1):11-17.

PCT International Preliminary Report on Patentability for PCT/US2005/030247 dated Feb. 28, 2007.

PCT International Search Report and Written Opinion for PCT/US2007/009379 dated Aug. 18, 2008.

PCT International Search Report and Written Opinion for PCT/US2006/047481 dated May 5, 2008.

PCT International Search Report and Written Opinion for PCT/US2007/011298 dated Jun. 25, 2008.

Su et al. "Testing of droplet-based microelectrofluidic systems", Proc. IEEE International Test Conference, pp. 1192-1200, 2003.

Chip mixes droplets faster, MIT Technology Review, Oct. 2003. Retrieved on Apr. 18, 2008 from: http://www. tmmag. com/Stories/2003/102203/Chip mixes_ droplets faster_ Brief_ 1 02203. html.

"Chip juggles droplets", Technology Research News, Sep. 4-11, 2002. Retrieved on Apr. 18, 2008 from: http://www.trnmag.com/Stories/2002/090402/Chip_juggles_droplets_090402.html.

"Laboratory on a Chip", Popular Mechanics—Tech Watch, p. 25, Mar. 2002. Retrieved on Apr. 18, 2008 from: http://www.ee.duke.edu/research/microfluidics/images/PopMechArticle.JPG.

"Making materials fit the future: accommodating relentless technological requirements means researchers must recreate and reconfigure materials, frequently challenging established laws of physics, while keeping an eye on Moore's law", R&D Magazine Conference Handout, Dec. 2001.

Agah, "DNA Analysis Chip by Electrowetting Actuation," Stanford Nanofabrication Facility, p. 9, 2002.

Bhansali et al., "Resolving chemical/bio-compatibility issues in microfluidic MEMS systems," SPIE Conference on Microfluidic Devices and Systems 11, vol. 3877, Santa Clara, CA, pp. 101-109 (1999).

Brady, "Electrowetting for DNA Sequencing on Chip," 2004 NNIN REU Research Accomplishments, pp. 26-27.

Fan, "Digital Microfluidics by Cross-Reference EWOD Actuation: Principle, Device, and System," PhD Dissertation, University of California Dept. of Mechanical Engineering, 2003.

Lehmann et al., "Droplet-Based DNA Purification in a Magnetic Lab-on-a-Chip," Angewandte Chemie, vol. 45, pp. 3062-3067, 2006.

Pamme, "Magnetism and microfluidics," Lab on a Chip (LOG), vol. 6, pp. 24-38, 2006.

Pipper et al., "Clockwork Pcr Including Sample Preparation," Angew. Chem. Int. Ed., vol. 47, pp. 3900-3904, 2008.

Raccurt et al., "On the influence of surfactants in electrowetting systems," J. Micromech. Microeng., vol. 17, pp. 2217-2223 (2007).

Roux and Fouillet, "3D droplet displacement in microfluidic systems by electrostatic actuation," Sensors and Actuators A, vol. 134, Issue 2, pp. 486-493, Mar. 15, 2007.

Taniguchi et al., "Chemical reactions in microdroplets by electrostatic manipulation of droplets in liquid media," Lab on a Chip, vol. 2, No. 2, pp. 19-23 (2002).

Torkkeli, "Droplet microfluidics on a planar surface," Doctoral Dissertation, Department of Electrical Engineering, Helsinki University of Technology (Oct. 3, 2003).

Verpoorte, "Beads and chips: new recipes for analysis," Lab on a Chip (LOG), vol. 3, pp. 60N-68N, 2003.

Chatterjee "Lab on a Chip Applications with a Digital Microfluidic Platform," UCLA Dissertation 2008, UMI Microform No. 3342975.

Washizu, "Electrostatic Actuation of Liquid Droplets for Micro-Reactor Applications", IEEE Industry Applications Society Annual Meeting, pp. 1867-1873, Oct. 5-9, 1997.

Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.

Wheeler, "Putting Electrowetting to Work," Science, vol. 322, No. 5901, pp. 539-540, Oct. 24, 2008.

Zhang et al., "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.

U.S. Appl. No. 12/465,935 Rule 1.132 Declaration Gaurav Jitendra Shah, Jun. 30, 2011.

Al-Rubeai, et al., "The effect of Pluronic F-68 on hybridoma cells in continuous culture", Applied Microbiology and Biology 1992, pp. 44-45.

Colgate and Matsumoto "An Investigation of Electrowetting-based Microactuation," Journal of Vacuum Science &Technology A-Vacuume Surfaces and Films, vol. 8 (4): pp. 3625-3633, Jul.-Aug. 1990.

Furdui et al., "Immunomagnetic T cell capture from blood for PCR analysis using microfluidic systems", Miniaturisation for Chemistry, Biology & Bioengineering, Lab Chip 2004, 4, 614-618.

Liu et al., "Effect of Non-Ionic Surfactants on the Formation of DNA/Emulsion Complexes and Emulsion-Medicated Gene Transfer", Pharmaceutical Research, pp. 1642-1646, vol. 13, No. 11, 1996.

Weber. et al. "Specific Blood Purification by Means of Antibody-Conjugated Magnetic Microspheres". Centre for Biomedical Technology. Austria. Scientific and Clinical Applications of Magnetic Carriers, 1997.

Fouillet et al. "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Paik et al. "A Digital-Microfluidic Approach to Chip Cooling," IEEE Design & Test of Computers, vol. 25, Jul. 2008, pp. 372-381.

Luan et al. "Integrated Optical Sensor in a Digital Microfluidic Platform," IEEE Sensors Journal, vol. 8, May 2008, pp. 628-635.

Yang et al. Manipulation of droplets in microfluidic systems, Trends in Analytical Chemistry, vol. 29, Feb. 2010; pp. 141-157.

Wulff-Burchfield et al. "Microfluidic platformversus conventional real-time polymerase chain reaction for the detection of Mycoplasma pneumonia in respiratory specimens.," Diagnostic Micobiology and Infectious disease, vol. 67, May 2010, pp. 22-29.

Barbulovic-Nad et al. A microfluidic platform for complete mammalian cell culture, Lab on a chip, vol. 10, Apr. 2010, pp. 1536-1542.

Office Action dated Oct. 9, 2009 from co-patented U.S. Appl. No. 11/639,710.

Response to Office Action dated Oct. 23, 2009 from co-patented U.S. Appl. No. 11/639,710.

Supplemental Response to Office Action dated Dec. 14, 2009 from co-patented U.S. Appl. No. 11/639,710.

Office Action dated Feb. 9, 2010 from co-patented U.S. Appl. No. 11/639,710.

Response to Office Action dated Feb. 16, 2010 from co-patented U.S. Appl. No. 11/639,710.

Office Action dated Feb. 25, 2010 from co-patented U.S. Appl. No. 11/639,710.

(56) References Cited

OTHER PUBLICATIONS

Response to Office Action dated Mar. 24, 2010 from co-patented U.S. Appl. No. 11/639,710.
Office Action dated Jun. 11, 2010 from related U.S. Appl. No. 11/912,913.
Office Action Nov. 1, 2010 from related U.S. Appl. No. 11/912,913.
Office Action dated Dec. 15, 2010 from related U.S. Appl. No. 11/912,913.
Office Action dated Mar. 18, 2011 from related U.S. Appl. No. 11/912,913.
Office Action dated Sep. 20, 2013 from related U.S. Appl. No. 11/912,913.
Office Action dated Oct. 7, 2014 from related U.S. Appl. No. 11/912,913.
Office Action dated Feb. 23, 2015 from related U.S. Appl. No. 11/912,913.
Office Action dated Sep. 16, 2016 from related U.S. Appl. No. 11/912,913.
Office Action dated Feb. 3, 2016 from related U.S. Appl. No. 11/912,913.
Zhang et al., "System Performance Evaluation with SystemC for Two PCR Microelectrofluidic Systems," Proceedings of the International Conference on Modeling and Simulation of Microsystems, San Juan, PR, pp. 48-53, Apr. 2002.
Aldrich et al., "PathoFinder: Microscale PCR Based Virus Detection," Yale Department of Engineering Design Course Report, Dec. 2003.
Kim et al., "Electrowetting-Driven Micropumping," UCLA Invention Report, Amendment, Declaration including Invention Report, Petition for Extension of Time, and Authorization to Charge Deposit, submitted to USPTO on Feb. 4, 2005.
Vinet et al., "Microarrays and microfluidic devices: miniaturized systems for biological analysis," Microelectronic Engineering 61-62 (2002) 41-47.
Cho et al., "Towards Digital Microfluidic Circuits: Creating, Transporting, Cutting and Merging Liquid Droplets by Electrowetting-Based Actuation," Proc. IEEE/Micro Electro Mechanical Systems Conference, pp. 32-35, 2002.
Seyrat and Hayes "Amorphous fluoropolymers as insulators for reversible low-voltage electrowetting," Journal of Applied Physics, vol. 90 (3): pp. 1383-1386, Aug. 1, 2001.
PCT International Preliminary Report on Patentability for PCT/US2006/018088 dated Nov. 14, 2007.
Merriam-Webster, definition of "substantial," attached, accessed Jul. 27, 2015, available at http://www.merriamwebster.com/dictionary/substantial.
Merriam-Webster, definition of "continuous," attached, accessed Jul. 27, 2015, available at http://www.merriamwebster.com/dictionary/continuous.
Su et al. (Concurrent Testing of Droplet-Based Microfluidic Systems for Multiplexed Biomedical Assays, Test Conference, 2004. Proceedings. ITC 2004. International, Oct. 28, 2004, pp. 883-892).
Chiou et al. (A Closed-Cycle Capillary Polymerase Chain Reaction Machine, Anal Chem. May 1, 2001;73(9):2018-21).
Nokano et al. (Single-molecule PCR using water-in-oil emulsion, J Biotechnol. Apr. 24, 2003;102(2):117-24).
Bu et al. (Design and theoretical evaluation of a novel microfluidic device to be used for PCR, J. Micromech. Microeng. 13 (Jun. 13, 2003) S125-S130).
Office action dated Sep. 21, 2011 from related U.S. Appl. No. 12/497,677.
Vaitkus et al., "Inhibition of cyclodextrin acid hydrolysis by some inclusion complexes," J. Ind Phenom Macrocycl Chem, 2010.
Wagner, "The Effects of Cyclodextrins on Guest Fluorescence," Ch. 2, Cyclodextrin Materials Photochemistry, Photophysics and Photobiology, 2006.
Henry, C., "Trapping Cells and Organelles", C&EN 83(10)7, Mar. 7, 2005.
Huebner A., et al., "Static Microdroplet Arrays", Lab-on-a-Chip, pp. 692-698, 2009.
Voznyi et al., A ftuorimetric enzyme assay for the diagnosis of MPS II (Hunter disease)), J. Inhert. Metab. Dis., vol. 17 24(6), pp. 675-680.
Office action dated Dec. 6, 2013 from related U.S. Appl. No. 13/862,587.
Office action dated Oct. 20, 2011 from related U.S. Appl. No. 12/531,844.
Office action dated May 29, 2013 from related U.S. Appl. No. 12/531,844.
Office action dated Mar. 11, 2013 from related U.S. Appl. No. 13/738,259.
Kolossvary, et al., "Molecular Dynamics Simulation of Cyclodextrin Inclusion Complexes in Enzymatic Lipid Hydrolysis", Biotechnology Letters, vol. 18, No. 4, Apr. 1996, pp. 440-444.
Wagner, Brian D., "The Use of Coumarins as Environmentally-Sensitive Fluorescent Probes of Heterogeneous Inclusion Systems", Molecules, vol. 14, No. 1, Jan. 6, 2009, pp. 210-237.
Office action dated Mar. 20, 2015 from related U.S. Appl. No. 14/116,544.
Office action dated Jul. 9, 2015 from related U.S. Appl. No. 14/116,544.
Balasubramanian, et al., "The use of concanavalin a in the purification or separation of multiple forms of brain hydrolases", J. Biosci, vol. 5, 1983, 61-64.
He, et al., "Purification and Characterization of Recombinant, Human Acid Ceramidase", The Journal of Biological Chemistry, 278 (35), 2003, 32978-32986.
Sparbier, et al., "Analysis of glycoproteins in human serum by means of glycospecific magnetic bead separation and LC-MALDI-TOF/TOF analysis with automated glycopeptide detection", Journal of biomolecular techniques: JBT, www.ncbi.nlm.nih.gov/pubmed/17916798, 2007, 252-258.
Watanabe et al., "Partial purification and properties of acid sphingornyelinase from rat liver", J. Lip. Research, 1983, vol. 24, 596-603.
Woodward, et al., "Affinity Chromatography of Beta-Glucosidase and Endo-Beta-Glucanase from Aspergillus niger on Concanavalin A-Sepharose: Implications for Cellulase Component Purification and Immobilization", Preparative Biochemistry, 16(4 ), 1986, 337-352.
Sista R. et al. Multiplex Newborn Screening for Pompe, Fabry, Hunter, Gaucher, and Hurler Diseases Using a Digital Microfluidic Platform. Clinica Chimica Acta 424:12-18, May 7, 2013.
International Search Report dated Nov. 29, 2012 from PCT International Application No. PCT/US2012/037036.
European Search Report and Opinion dated Jan. 5, 2015 from European Application No. 12781874.8
Office action dated Jun. 13, 2013 from related U.S. Appl. No. 13/470,919.
Office action dated Oct. 21, 2013 from related U.S. Appl. No. 13/470,919.
Office action dated Jan. 11, 2006 from related U.S. Appl. No. 14/399,051.
Kunugi et al. n-d-biotinyl-7-amino-4-methylcoumarin as a novel fluorigenic substrate for the determination of biotinidase activity; Chemistry Letters (1997) pp. 391-392.
Wastell et al. A Sensitive Fluorimetric Rate Assay for Biotinidase Using a New Derivative of Biotin, Biotinyl-6-Aminoquinoline; Analytical Biochemistry, vol. 140 (1984) pp. 69-73.
Wallac, Oy. 51 O(K) Summary; (Mar. 5, 2010) downloaded from http://www.accessdata.fda.gov/cdrh_docs/pdf9/K090123.pdf on Nov. 10, 2015.

\* cited by examiner

DROPLET ACTUATORS AND TECHNIQUES FOR DROPLET-BASED ENZYMATIC ASSAYS

1 RELATED APPLICATIONS

This application is a 35 U.S.C. 371 U.S. National Stage Entry of International Application No. PCT/US2012/04633 having an international filing date of Jul. 11, 2012, the application of which claims the benefit of provisional U.S. Patent Application No. 61/506,369 filed on Jul. 11, 2011 and 61/506,359, filed on Jul. 11, 2011.

2 GRANT INFORMATION

This invention was made with government support under HG004354 awarded by the National Institutes of Health of the United States.

3 FIELD OF THE INVENTION

The invention relates to a droplet actuator with a modified droplet operations surface.

4 BACKGROUND

A droplet actuator typically includes one or more substrates configured to form a surface or gap for conducting droplet operations. The one or more substrates establish a droplet operations surface or gap for conducting droplet operations and may also include electrodes arrange to conduct the droplet operations. The droplet operations substrate or the gap between the substrates may be coated or filled with a filler fluid that is immiscible with the liquid that forms the droplets.

Droplet actuators are used in a variety of applications, including molecular diagnostic assays, such as enzymatic assays. In one example, lysosomal enzyme tests used in newborn testing assays (NBS) may be performed on a droplet actuator. The NBS assays are fluorescent based tests which measure the release of 4-methylumbelliferone (4-MU) or other umbelliferyl derivatives (e.g., 6-hexadecanoylamido-4-methylumbelliferone; HMU) after enzymatic hydrolysis of the substrates. In the droplet operations environment of a droplet actuator, partitioning of 4-MU (or derivatives) between the aqueous phase (i.e., droplet) and the organic phase (filler fluid) may result in a reduction in the assay signal and potential contamination of neighboring samples. Therefore, there is a need for improved methods for reducing partitioning of 4-MU (or derivatives) in droplet-based bioassays on a droplet actuator.

5 SUMMARY OF THE INVENTION

The invention provides a method of conducting an assay. The method may, for example, include incubating a droplet in oil, the droplet including an umbelliferone substrate, a sample potentially including an enzyme which cleaves the umbelliferone substrate, and a zwitterionic surfactant, and detecting a signal emitted from the droplet.

In certain embodiments, the droplet further includes a cyclodextrin compound. In certain embodiments, the cyclodextrin compound is selected from the group consisting of α-cyclodextrins, β-cyclodextrins, and γ-cyclodextrins, and analogs and derivatives of the foregoing. In some cases, the umbilliferone substrate is selected from the group consisting of alkylumbelliferyl-α-L-iduronides, 4-methylumbelliferyl-α-L-iduronide, 4-methylumbelliferyl-α-L-iduronide-2-sulfate, 4-methylumbelliferyl-α-L-idopyranosiduronic acid, 4-methylumbelliferyl-α-L-fucoside, 4-methylumbelliferyl-α-L-mannoside, 4-methylumbelliferyl-β-D-mannoside, 4-methylumbelliferyl β-D-N-acetylglucosaminide, 4-methylumbelliferyl β-D-N-acetylglucosaminide sulfate, alkylumbelliferyl-β-D-glycosides, methylumbelliferyl-β-D-glycosides, 4-methylumbelliferyl-α-D-galactoside, 4-methylumbelliferyl-β-D-galactoside, 4-methylumbelliferyl-β-D-glucouronic acid, phenolphthalein-β-D-glucuronic acid, ethylumbelliferyl-β-D-glycosides, multrifluoroethylumbelliferyl-β-D-glycosides, pentafluoroethylumbelliferyl-β-D-glycosides, pentafluoroethylumbelliferyl-β-D-glucoside, umbelliferylchiotriosides, 4-alkyumbelliferylchiotrioside, 4-methylumbelliferyl-chiotrioside, 4-methylumbelliferyl-β-galactose, 4-alkyumbeliferrone phosphates, 4-methylumbeliferrone phosphate, 6-alkanoylamido-4-methylumbelliferones, substrates including a 4-methyllumbelliferyl group, 6-hexadecanoylamido-4-methylumbelliferone, 4-methyllumbelliferyl-β-D-glucosaminide, 4-methylumbelliferyl-α-neuraminic acid, 4-methylumbelliferyl-α-D-N-acetylgalactosaminide, and their functional analogs and derivatives. In certain embodiments, the steps are performed within droplets controlled by a droplet actuator. In certain embodiments, the droplet actuator controls the steps using electrode mediated droplet operations. In certain embodiments, the droplet actuator controls the steps using electrowetting mediated droplet operations. In certain embodiments, the droplet actuator controls the steps using dielectrophoresis mediated droplet operations.

The invention provides a method of conducting a droplet-based enzyme assay. For example, the method may include providing an immiscible fluid including a sample droplet including an enzyme of interest, and one or more reagent droplets including a substrate which is potentially modified in the presence of the enzyme yielding one or more signal-producing products, a zwitterionic surfactant, and optionally, other reagents sufficient to produce the activity of the target enzyme under ordinary conditions. The method may include combining the sample droplet and the one or more reagent droplets in the immiscible fluid to yield a reaction droplet effecting an enzyme reaction in the immiscible fluid, and measuring any signal produced by the one or more signal producing products. In certain embodiments, the zwitterionic surfactant is selected form the group consisting of n-Octylphosphocholine, n-Nonylphosphocholine, n-decylphosphocholine, n-dodecylphosphocholine, 3-cyclohexyl-1-propylphosphocholine, decylphospho-N-methylethanolamine, n-decyl-N,N-dimethylglycine, n-octyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, dimethylbenzylammonium propane sulfonate, 3-[(3-Cholamidopropyl)-dimethylammonio]-1-propane sulfonate, and 3-[(3-cholamidopropyl)-dimethylammonio]-2-hydroxy-1-propanesulfonate.

The invention provides a method of providing diagnostic information, the method including conducting an assay according to a method of the invention, wherein the sample droplet includes a clinical sample from a subject, the sample including the enzyme of interest, and providing to the subject diagnostic information based on the activity of the enzyme of interest from the human clinical sample. In certain embodiments, the diagnostic information includes information diagnostically relevant to a glycogen storage disease. In certain embodiments, the assay is conducted and the diagnostic information is provided at a point of sample collection. In certain embodiments, the point of sample collection is in the presence of the subject. In certain embodiments, the clinical sample includes a sample substance selected from the group consisting of: blood, plasma, serum, tears, saliva, and urine. In certain embodiments, the clinical sample includes a dried blood sample. In certain embodiments, the clinical sample includes a fresh blood sample. In certain embodiments, the fresh blood sample is collected from the subject and immediately loaded onto a droplet actuator for conducting the assay. In certain embodiments, time from collection of the blood sample to providing diagnostic information is less than about 12 hours. In certain embodiments, time from collection of the blood sample to providing diagnostic information is less than about 6 hours. In certain embodiments, the clinical sample includes a human clinical sample. In certain embodiments, the clinical sample includes a non-human animal clinical sample. In certain embodiments, the substrate includes a glycoside substrate. In certain embodiments, the substrate releases a fluorophore upon contact with the enzyme of interest. In certain embodiments, two or more assays are conducted simultaneously using different fluorophores for each enzyme tested. In certain embodiments, the fluorophore includes 4-methylumbelliferyl. In certain embodiments, the substrate includes a glycoside substrate which releases a fluorophore upon contact with the enzyme of interest. In certain embodiments, the substrate includes a glycoside substrate including glucose, galactose, fucose, mannose, sialic acid, hexose, hexosamine and/or N-acetylated hexosamine. In certain embodiments, the substrate includes a 4-methylumbelliferyl glycoside. In certain embodiments, the method further includes reducing or eliminating reaction contaminants associated with the substrate prior to yielding the assay droplet. In certain embodiments, the reducing or eliminating reaction contaminants includes photobleaching the substrate prior to yielding the assay droplet. In certain embodiments, the photobleaching is effected prior to providing the droplet including the substrate on the droplet actuator. In certain embodiments, the photobleaching is effected after to providing the droplet including the substrate on the droplet actuator. In certain embodiments, the substrate includes a 4-methylumbelliferyl glycoside substrate. In certain embodiments, the method includes photobleaching the substrate prior to yielding the assay droplet. In certain embodiments, the immiscible liquid includes a filler fluid. In certain embodiments, the immiscible liquid includes a silicone oil. In certain embodiments, the filler fluid includes a surfactant. In certain embodiments, the surfactant includes nonionic low hydrophile-lipophile balanced (HLB) surfactant. In certain embodiments, the HLB is less than about 10. In certain embodiments, the HLB is less than about 5. In certain embodiments, the surfactant is selected from the group consisting of Triton X-15, Span 85, Span 65, Span 83, Span 80, Span 60, and fluorinated surfactants. In certain embodiments, the sample droplet includes a reconstituted blood sample, the blood sample is reconstituted using a single universal reconstitution solution, the blood sample is divided to yield two or more reaction droplets, and two or more of the reaction droplets are each combined with one or more sets of one or more reagent droplets, each such set including reagents selected for establishing reaction conditions for a different enzyme assay. In certain embodiments, the universal reconstitution solution includes a saline solution. In certain embodiments, the universal reconstitution solution includes water. In certain embodiments, the enzyme assay is selected to provide diagnostic information about an enzyme deficiency. In certain embodiments, the enzyme deficiency is selected from lysosomal storage diseases. In certain embodiments, the enzyme deficiency is selected from the group consisting of Pompe, Niemann-Pick, Fabry, Krabbe, and Gaucher. In certain embodiments, the method also includes providing therapeutic treatment to a subject based on the diagnostic information. In certain embodiments, the sample droplet including an enzyme of interest includes cultured cells and/or supernatant from a cell culture. In certain embodiments, the substrate is selected from the group consisting of 4-methylumbelliferyl-α-L-iduronide, 4-methylumbelliferyl-β-D-galactoside, 4-methylumbelliferyl-β-D-glucuronic acid, 4-methylumbelliferyl-α-L-fucoside, 4-methylumbelliferyl-α-mannoside, 4-methylumbelliferyl-β-D-mannoside, 4-nitrocathecol sulfate, 4-methylumbelliferyl-β-D-N-acetylglucosaminide, 4-methylumbelliferyl-β-D-N-acetylglucosaminide sulfate, 4-methylumbelliferyl-β-D-glucosaminide, 4-methylumbelliferyl-α-D-galactoside, 4-methylumbelliferyl-α-D-neuraminic acid, 4-methylumbelliferyl-α-D-N-acetylgalactosaminide, phenolphthalein β-D-glucuronic acid, and mixtures and derivatives thereof. In certain embodiments, the substrate includes a fluorophoric moiety. In certain embodiments, the fluorophoric moiety includes 4-methyllumbelliferyl. In certain embodiments, the substrate includes a chromophoric moiety. In certain embodiments, the chromophoric moiety includes 4-nitrocathecol or phenolphthalein. In certain embodiments, the substrate includes a radioactive moiety. In certain embodiments, the radioactive moiety includes 14C sphingomyelin or 3H galactosylceramide. In certain embodiments, incubating the reaction droplet for a period of less than about 12 hours.

The invention provides a method of conducting an assay in a droplet in oil, the droplet including a lipophilic moiety, the method including in the droplet a nonionic surfactant selected from the group consisting of n-hexyl-β-D-glucopyranoside, 2-cyclohexyl-1-ethyl-β-D-maltoside, 3-cyclohexyl-1-propyl-β-D-maltoside, octanoyl-N-methylglucamide, nonanoyl-N-methylglucamide, octanoyl-N-hydroxyethylglucamide, nonanoyl-N-hydroxyethylglucamide, n-hexyl-β-D-glucopyrano side, and α-[4-(1,1,3,3-tetramethylbutyl)phenyl]-ω-hydroxy-poly (oxy-1,2-ethanediyl). In certain embodiments, the lipophilic moiety includes an umbilliferone substrate. In certain embodiments, umbilliferone substrate is selected from the group consisting of alkylumbelliferyl-α-L-iduronides, 4-methylumbelliferyl-α-L-iduronide, 4-methylumbelliferyl-α-L-iduronide-2-sulfate, 4-methylumbelliferyl-α-L-idopyranosiduronic acid, 4-methylumbelliferyl-α-L-fucoside, 4-methylumbelliferyl-α-L-mannoside, 4-methylumbelliferyl-β-D-mannoside, 4-methylumbelliferyl β-D-N-acetylglucosaminide, 4-methylumbelliferyl β-D-N-acetylglucosaminide sulfate, alkylumbelliferyl-β-D-glycosides, methylumbelliferyl-β-D-glycosides, 4-methylumbelliferyl-α-D-galactoside, 4-methylumbelliferyl-β-D-galactoside, 4-methylumbelliferyl-β-D-glucouronic acid, phenolphthalein-β-D-glucuronic acid, ethylumbelliferyl-β-D-glycosides, multrifluoroethylumbelliferyl-β-D-glycosides, pentafluoroethylumbelliferyl-β-D-glycosides, pentafluoroethylumbelliferyl-β-D-glucoside, umbelliferylchiotriosides, 4-alkyumbelliferylchiotrioside, 4-methylumbelliferylchiotrioside, 4-methylumbelliferyl-β-galactose, 4-alkyumbeliferrone phosphates, 4-methylumbeliferrone phosphate, 6-alkanoylamido-4-methylumbelliferones, substrates including a 4-methyllumbelliferyl group, 6-hexadecanoylamido-4-methylumbelliferone, 4-methyllumbelliferyl-β-D-glucosaminide, 4-methylumbelliferyl-α-neuraminic acid, 4-methylumbelliferyl-α-D-N-acetylgalactosaminide, and their functional analogs and derivatives.

The invention provides a droplet actuator including one or more substrates arranged to form a droplet operations gap, a fluoropolymer surface on one or more droplet operations gap-facing surfaces of the one or more substrates, where the fluoropolymer surface is deposited using a plasma-enhanced chemical vapor deposition process, a perfluorinated oil filler fluid in the droplet operations gap. In certain embodiments, the fluoropolymer surface includes an amorphous fluoropolymer. In certain embodiments, the fluoropolymer surface includes an amorphous fluoropolymer including carboxyl end-groups. In certain embodiments, the fluoropolymer surface includes an amorphous fluoropolymer including aminosilane coupling agents. In certain embodiments, the fluoropolymer surface includes an amorphous fluoropolymer including perfluoro groups. In certain embodiments, the fluoropolymer surface includes CYTOP® Type A. In certain embodiments, the fluoropolymer surface includes CYTOP® Type M. In certain embodiments, the fluoropolymer surface includes CYTOP® or Type S. In certain embodiments, the one or more substrates comprise one or more electrodes arranged for conducting droplet operations. In certain embodiments, the one or more substrates comprise an arrangement of electrodes arranged for conducting electrowetting-mediated droplet operations. In certain embodiments, the one or more substrates includes a printed circuit board substrate. In certain embodiments, the one or more substrates includes a silicone substrate. In certain embodiments, the one or more substrates includes a glass substrate. In certain embodiments, a droplet in the droplet operations gap, the droplet including a lipophilic substance. In certain embodiments, the water contact angle (θ) of the surface is greater than about 100.

6 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current.

Any suitable voltage may be used. For example, an electrode may be activated using a voltage which is greater than about 150 V, or greater than about 200 V, or greater than about 250 V, or from about 275 V to about 1000 V, or about 300 V. Where alternating current is used, any suitable frequency may be employed. For example, an electrode may be activated using alternating current having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based Applications," published on Jul. 20, 2006; the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim and/or Shah et al., U.S. patent application Ser. No. 10/343,261, entitled "Electrowetting-driven Micropumping," filed on Jan. 27, 2003, Ser. No. 11/275,668, entitled "Method and Apparatus for Promoting the Complete Transfer of Liquid Drops from a Nozzle," filed on Jan. 23, 2006, Ser. No. 11/460,188, entitled "Small Object Moving on Printed Circuit Board," filed on Jan. 23, 2006, Ser. No. 12/465,935, entitled "Method for Using Magnetic Particles in Droplet Microfluidics," filed on May 14, 2009, and Ser. No. 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," Lab Chip, 10:832-836 (2010); the entire disclosures of which are incorporated herein by reference, along with their priority documents. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the invention. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be from about 5 µm to about 600 µm, or about 100 µm to about 400 µm, or about 200 µm to about 350 µm, or about 250 µm to about 300 µm, or about 275 µm. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the invention include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the invention. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the invention may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or perfluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene)poly(styrenesulfonate) (PEDOT: PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness in the range of about 20 to about 200 nm, preferably about 50 to about 150 nm, or about 75 to about 125 nm, or about 100 nm. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MIT- SUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the invention may derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the invention includes those described in Meathrel, et al., U.S. Pat. No. 7,727,466, entitled "Disintegratable films for diagnostic devices," granted on Jun. 1, 2010.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×- 3×-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be a low-viscosity oil, such as silicone oil or hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the invention are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Reservoir" means an enclosure or partial enclosure configured for holding, storing, or supplying liquid. A droplet actuator system of the invention may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the invention, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

7 BRIEF DESCRIPTION OF THE DRAWINGS

8 DESCRIPTION

Figure 1:
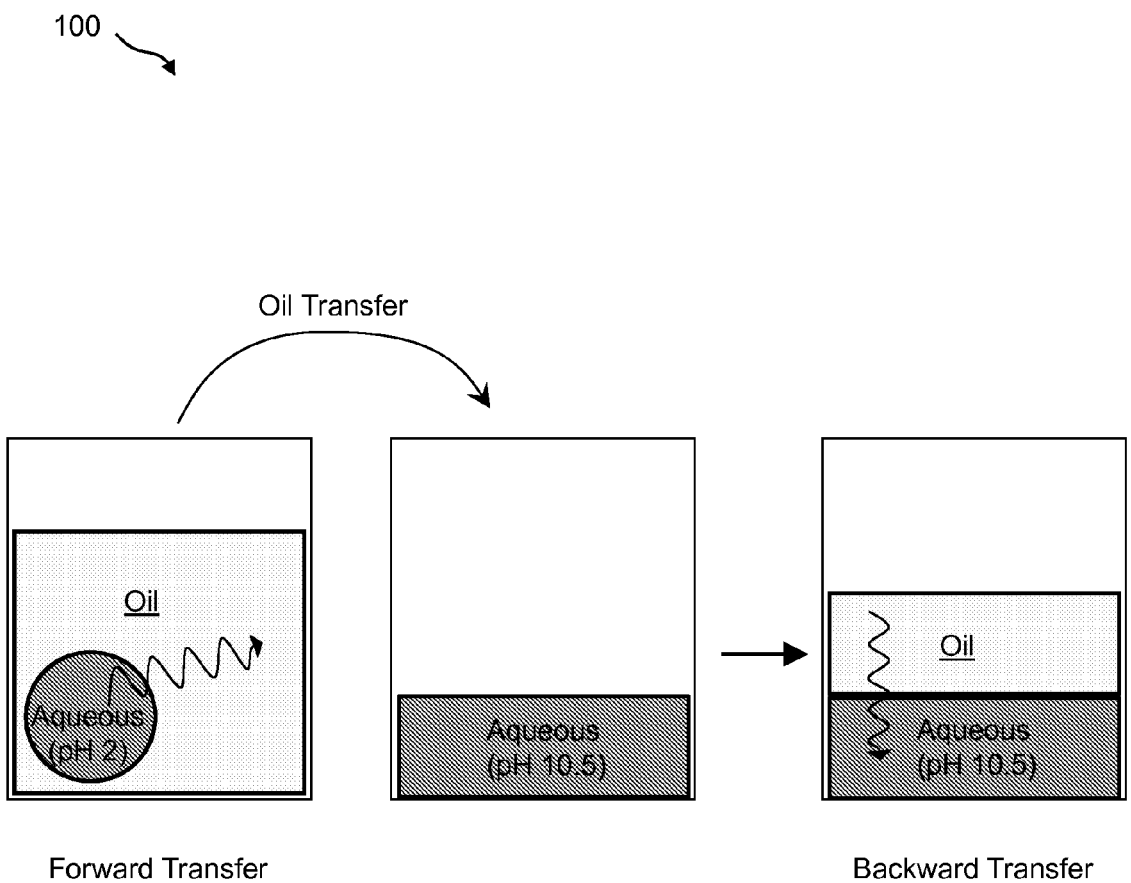
FIG. 1 shows a diagram of an example of an on-bench assay protocol for evaluating the effect of aqueous surfactants on 4-MU partitioning.

The present invention provides methods to reduce, preferably substantially or entirely eliminate, partitioning of 4-MU (or derivatives) in droplet-based bioassays on a droplet actuator. In one embodiment, surfactants (detergents) may be used to retain 4-MU (or derivatives) within an aqueous phase droplet. The methods of the invention provide significantly improved signal retention and substantially reduced cross-contamination between droplets. The methods of the invention also provide significantly improved discrimination between a positive signal and a negative signal in 4-MU-based bioassays.

Further, the invention provides a droplet actuator with a droplet operations surface having a hydrophobic coating that is chemically compatible with the perfluorinated oil (or solvents) and that also ensure suitable droplets operations performance. The invention provides methods of depositing hydrophobic coatings on the droplet operations surfaces of a droplet actuator to render them suitable for use with perfluorinated solvents. The invention also provides hydrophobic coatings for improving operations performance. For example, the invention provides droplet actuators with coatings applied by liquid deposition processes as well as coatings applied by plasma-enhanced chemical vapor deposition (PECVD)-based processes.

8.1 Reducing Partitioning of 4-MU

4-MU-containing substrates (a.k.a 7-hydroxy 4-methylcoumarin) are used in a number of fluorometric enzyme assays (e.g., enzymatic assays for the detection of lysosomal storage disorders in newborns). The fluorometric enzyme assays are based on the hydrolysis of a 4-MU-containing substrate by a specific enzyme to yield the fluorescent molecule 4-MU. In the droplet operations environment of a droplet actuator, partitioning of 4-MU between the aqueous phase (i.e., droplet) and the organic phase (filler fluid) may result in a reduction in the assay signal and potential contamination of neighboring samples. The enzymatic turnover of the 4-MU substrate requires a low-pH environment (acidic environment). At low pH (pK of 4-MU=7.9), 4-MU is non-ionic and hydrophobic and partitions preferentially from the aqueous droplet phase into the oil filler phase (100:1). Droplets subsequently prepared for the detection step of the bioassay are at a high pH. Fluorescence of 4-MU is optimal at elevated pH (pH>10). A high pH (pH>10) facilitates reverse partitioning of 4-MU from the oil phase back into an aqueous phase droplet. The potential for droplet cross-contamination occurs when an acidic droplet with elevated enzyme concentration (producing significant amounts of 4-MU product) is in proximity of a basic droplet with substantially lower 4-MU concentrations.

The efficacy of different surfactants (detergents) in containing 4-MU (or derivatives) within an aqueous phase may, for example, be evaluated using a partitioning assay. Parameters that may be varied in the assay for evaluation of surfactants in aqueous containment of 4-MU (or derivatives) include, but are not limited to, the pH of the aqueous phase solution, and the critical micelle concentration of the surfactant.

FIG. 1 shows a diagram of an example of an on-bench assay protocol 100 for evaluating the effect of aqueous surfactants on 4-MU partitioning. The assay format includes forward transfer partitioning (forward extraction; FE) of 4-MU from an aqueous phase to an oil phase and backward transfer partitioning (backward extraction; BE) of 4-MU from an oil phase to an aqueous phase. The assay is performed in 96-well microtiter substrates; clear 96-well substrates (e.g., Costar 3631) for evaluation of forward transfer partitioning with bottom probe fluorescence detection and solid black 96-well substrates (e.g., Costar 3915) for evaluation of backward transfer partitioning with top probe fluorescence detection. A BioTek Synergy HT instrument with 3 mm top probe and 5 mm bottom probe, may, for example, be used for fluorescence measurements.

An example of an assay format used for testing the effect of surfactants on contamination through 4-MU partitioning includes, but is not limited to, the following steps: Pipette an aliquot (20 μL) of an aqueous phase solution (e.g., at pH 2 to pH 10.5) containing 0.01% Tween® 20 in a well of a 96-well clear microtiter plate. The aqueous phase solution may also include 4-MU (e.g., 100 μM), NaCl (e.g., 50 mM), and BSA (e.g., 1 mg/mL). Add 130 μL of oil (e.g., silicone oil 5 cSt, 0.1% Triton X-15) to each well that contains an aqueous phase droplet. Seal the plate with aluminum foil and shake using a bench top shaker (e.g., Thermofisher shaker at speed setting 5) for 30 min at room temperature. Carefully remove the aluminum foil and observe each well to note and record any defects in droplet quality (minimize light exposure during this step). Measure the fluorescence of each well using a bottom probe at gains 40, 45, and 50. Transfer, without disturbing the aqueous droplet, 75 μL of the oil phase (FE oil) from each well into the respective well of a solid black microtiter plate that contains 75 μL of 200 mM NaHCO$_3$ in each well. Seal the plate with aluminum foil and shake using, for example, a Thermofisher bench top shaker (e.g., speed setting 5) for 60 min at 40° C. Remove the aluminum foil and measure the fluorescence of each well using a top probe at gains 50, 60, 70, and 80.

Figure 2:
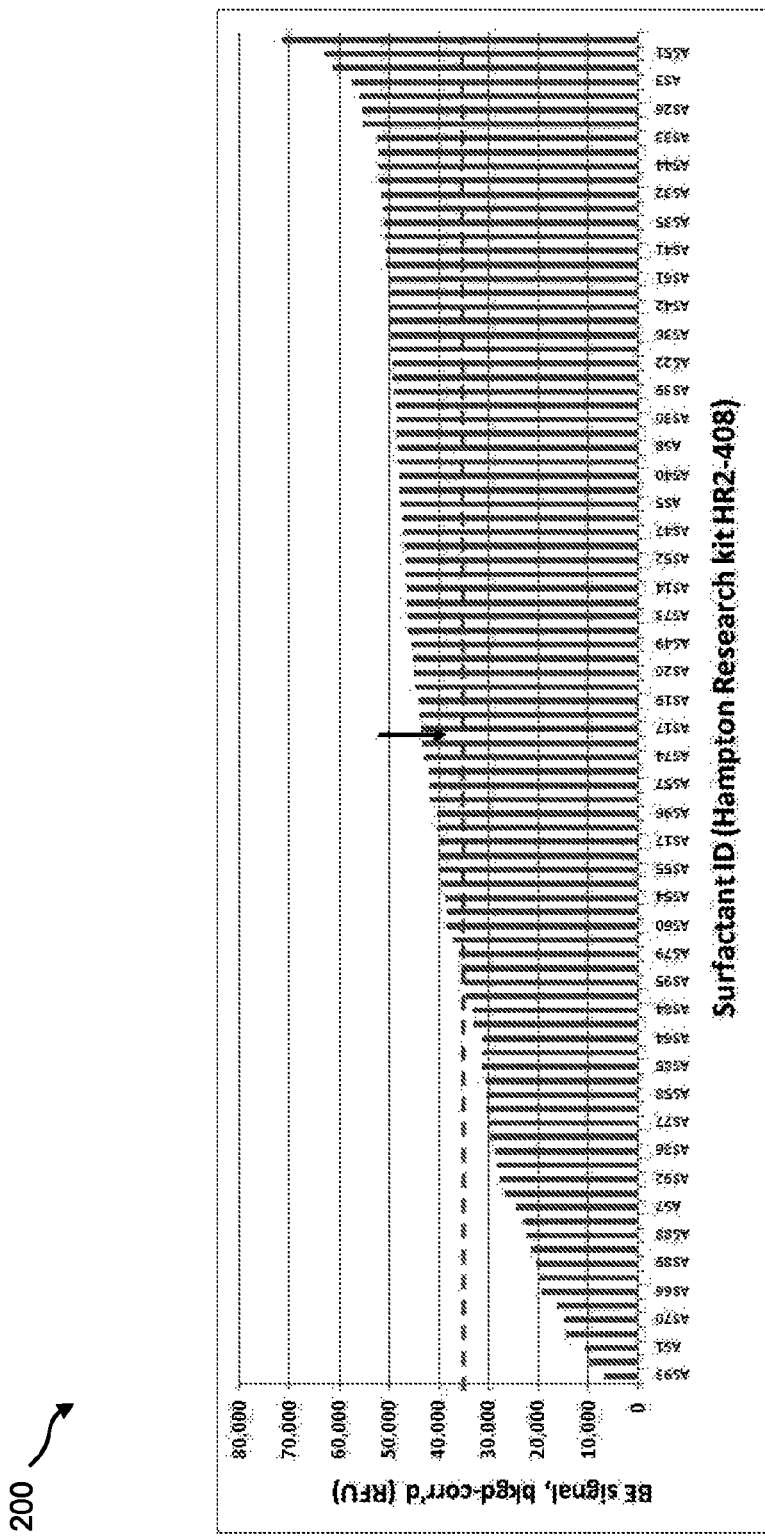
FIG. 2 shows an example of a plot of relative fluorescence readings for backward transfer partitioning (backward extraction; BE) of a 4-MU partitioning assay used to evaluate the effect of aqueous phase surfactants on 4-MU containment.

FIG. 2 shows a bar graph 200 of relative fluorescence readings for backward transfer partitioning (backward extraction; BE) of a 4-MU partitioning assay used to evaluate the effect of aqueous phase surfactants on 4-MU containment. In this example, surfactants were selected from an array of different surfactants available in the detergent screening kit HR2-408 from Hampton Research, Inc. The experiment was performed using 5 cSt silicone oil with 0.1% w/v Triton X-15 as the organic phase (oil phase). Each surfactant was used at 1.5 times the surfactant's critical micellar concentration (CMC). The identity of each surfactant is listed in Tables 1 and 2. AS17 (ANAPOE®-20 or Tween® 20) was used as a reference signal (43,000-44,000 RFU) and reflects an example of the level of droplet cross-contamination that may be observed in a 4-MU-based bioassay (e.g., newborn screening assay) performed on a droplet actuator. Surfactants that retained 4-MU more efficiently than AS17 (ANAPOE®-20 or Tween® 20), i.e., to the left of the arrow in FIG. 2, are listed in Table 1. Surfactants that were less efficient than AS17 in retaining 4-MU, i.e., to the right of the arrow in FIG. 2, are listed in Table 2.

TABLE 1

Aqueous surfactants (AS) in 4-MU retention assay of FIG. 2 (left of arrow)

| AS # | Surfactant | AS # | Surfactant |
|---|---|---|---|
| AS 93 | FOS-Choline ®-8 | AS 64 | HEGA ®-9 |
| AS 91 | ZWITTERGENT ® 3-10 | AS 63 | C-HEGA ®-10 |
| AS 1 | BAM | AS 84 | DDMAB |
| AS 90 | FOS-Choline ®-9 | AS 81 | FOS-Choline ®-8, fluorinated |
| AS 70 | n-Hexyl-β-D-glucopyranoside | AS 95 | LysoFos ™ Choline 12 |
| AS 69 | CYMAL ®-2 | AS 2 | n-Dodecyl-β-iminodipropionic acid, |
| AS 66 | MEGA-8 | AS 79 | n-Dodecyl-N,N-dimemylglycine |
| AS 68 | HEGA ®-8 | AS 82 | n-Undecyl-N,N-Dimethlamine-oxide |
| AS 89 | n-Decyl-N,N-dimethylglycine | AS 60 | n-Heptyl-β-D-thioglucopyranoside |
| AS 67 | HEGA ®-9 | AS 25 | ANAPOE ®-C$_{12}$E$_{10}$ |
| AS 88 | FOS-Choline ®-10 | AS 54 | Pluronic ® F-68 |
| AS 83 | ZWITTERGENT ® 3-12 | AS 53 | C-HEGA ®-11 |
| AS 7 | Sodium cholate | AS 55 | HECAMEG ® |
| AS 9 | ANAPOE ®-X-305 | AS 29 | ANAPOE ®-X-405 |
| AS 92 | CYCLOFOS ™-3 | AS 17 | ANAPOE ®-20 (Tween ® 20) |
| AS 62 | CYMAL ®-3 | AS 56 | n-Octyl-β-D-glucoside |
| AS 86 | CHAPS | AS 96 | LysoFos ™ Choline 10 |
| AS 94 | ZWITTERGENT ® 3-08 | AS 59 | 2,6-Dimethyl-4-heptyl-β-D-malto- |
| AS 77 | NDSB-256 | AS 57 | n-Octanoylsucrose |
| AS 80 | FOS-Choline ®-12 | AS 31 | ANAPOE ®-C$_{10}$E$_6$ |
| AS 58 | MEGA-9 | AS 74 | NDSB-201 |
| AS 87 | CHAPSO | AS 12 | ANAPOE ®-58 |
| AS 85 | FOS-MEA ®-10 | | |
| AS 78 | ZWITTERGENT ® 3-14 | | |

TABLE 2

Aqueous surfactants (AS) in 4-MU retention assay of FIG. 2 (right of arrow)

| AS # | Surfactant | AS # | Surfactant |
|---|---|---|---|
| AS 17 | ANAPOE ®-20 (Tween ® 20) | AS 21 | ANAPOE ®-C$_{12}$E$_8$ |
| AS 34 | ANAPOE ®-C$_{10}$E$_9$ | AS 22 | n-Dodecyl-β-D-maltoside |
| AS 35 | ANAPOE ®-35 | AS 75 | NDSB-211 |
| AS 24 | ANAPOE ®-X-114 | AS 36 | n-Decyl-β-D-maltoside |
| AS 20 | ANAPOE ®-C$_{13}$E$_8$ | AS 11 | n-Hexadecyl-β-D-maltoside |
| AS 76 | NDSB-221 | AS 42 | n-Nonyl-β-D-maltoside |
| AS 49 | n-Octyl-β-D thiomaltoside | AS 50 | n-Octyl-β-D-thioglucoside |
| AS 10 | IPTG | AS 61 | n-Octyl-β-D-galactopyranoside |
| AS 73 | NDSB-195 | AS 37 | LDAO |
| AS 71 | C-HEGA ®-8 | AS 41 | CYMAL ®-5 |
| AS 14 | ANAPOE ®-80 | AS 38 | n-Decanoylsucrose |
| AS 4 | CTAB | AS 35 | Big CHAP, deoxy |
| AS 52 | DDAO | AS 6 | Sodium dodecyl sulfate |
| AS 72 | CYMAL ®-2 | AS 32 | n-Decyl-β-D-thiomaltoside |
| AS 47 | CYMAL ®-4 | AS 18 | Thesit ® |
| AS 16 | ANAPOE ®-C$_{12}$E$_9$ | AS 44 | HEGA ®-10 |

TABLE 2-continued

Aqueous surfactants (AS) in 4-MU retention assay of FIG. 2 (right of arrow)

| AS # | Surfactant | AS # | Surfactant |
|---|---|---|---|
| AS 5 | Deoxycholic acid, sodium salt | AS 28 | n-Undecyl-β-D-maltoside |
| AS 45 | MEGA-10 | AS 33 | Octyl maltoside, fluorinated |
| AS 40 | n-Nonyl-β-D-thiomaltoside | AS 23 | CYMAL ®-7 |
| AS 15 | n-Tridecyl-β-D-maltoside | AS 26 | Sucrose monolaurate |
| AS 8 | Sodium dodecanoyl sarcosine | AS 27 | CYMAL ®-6 |
| AS 43 | n-Nonyl-β-D-glucoside | AS 3 | Dodecyltrimethylammonium chloride |
| AS 30 | TRITON ® X-100 | AS 46 | $C_8E_5$ |
| AS 13 | n-Tetradecyl-β-D-maltoside | AS 51 | Hexaethylene glycol monooctyl ether |
| AS 39 | n-Nonyl-β-D-thioglucoside | AS 48 | $C_8E_4$ |

Classification of the most efficient surfactants (detergents) in retaining 4-MU in an aqueous droplet is shown in Table 3. The zwitterionic surfactant group (14) includes sulfobetaines, betaine and lipid-like phosphocholine and phosphoethanolamine. The non-ionic surfactant group (9) includes sugar-based surfactants (glycosides, glucamides).

TABLE 3

Classification of top 25 aqueous surfactants in 4-MU retention assay (<32,000 RFU)

| AS # | Surfactant | Type | Chemical Class |
|---|---|---|---|
| AS 93 | FOS-Chorine ®-8 | Zwitterionic | Alkyl phosphocholine |
| AS 91 | ZWITTERGENT ® 3-10 | Zwitterionic | Alkyl sulfobetaine |
| AS 1 | BAM | Cationic | Quaternary ammonium |
| AS 90 | FOS-Chorine ®-9 | Zwitterionic | Alkyl phosphocholine |
| AS 70 | n-Hexyl-β-D-glucopyranoside | Non-Ionic | Alkyl glycoside† |
| AS 69 | CYMAL ®-2 | Non-Ionic | Cycloalkyl glycoside† |
| AS 66 | MEGA-8 | Non-Ionic | Alkanoyl-N-methylglucamide*† |
| AS 68 | HEGA ®-8 | Non-Ionic | Alkanoyl-N-hydroxyethylglucamide*† |
| AS 89 | n-Decyl-N,N-dimethylglycine | Zwitterionic | Alkyl betaine |
| AS 67 | C-HEGA ®-9 | Non-Ionic | Cycloalkanoyl hydroxyethylglucamide† |
| AS 88 | FOS-Choline ®-10 | Zwitterionic | Alkyl phosphocholine |
| AS 83 | ZWITTERGENT ® 3-12 | Zwitterionic | Alkyl sulfobetaine |
| AS 7 | Sodium cholate | Anionic | Bile salts |
| AS 9 | ANAPOE ®-X-305 | Non-Ionic | Polyoxyethylene |
| AS 92 | CYCLOFOS ™-3 | Zwitterionic | Cycloalkyl phosphocholine |
| AS 62 | CYMAL ®-3 | Non-Ionic | Cycloalkyl glycoside† |
| AS 86 | CHAPS | Zwitterionic | Sulfobetaine |
| AS 94 | ZWITTERGENT ® 3-08 | Zwitterionic | Alkyl sulfobetaine |
| AS 77 | NDSB-256 | Zwitterionic | Non-detergent sulfobetaine |
| AS 80 | FOS-Choline ®-12 | Zwitterionic | Alkyl phosphocholine |
| AS 58 | MEGA-9 | Non-Ionic | Alkanoyl-N-methylglucamide*† |
| AS 87 | CHAPSO | Zwitterionic | Sulfobetaine |
| AS 85 | FOS-MEA ®-10 | Zwitterionic | Lipid-like (phosphoethanolamine) |
| AS 78 | ZWITTERGENT ® 3-14 | Zwitterionic | Alkyl sulfobetaine |
| AS 64 | HEGA ®-9 | Non-Ionic | Alkanoyl-N-hydroxyethylglucamide*† |

*Fatty acid glucamide or alkanoyl glucamide;
†Sugar-based surfactants

8.2 Assay Methods

Enzymatic indicators of lysosomal storage diseases (LSDs) can be identified using droplet based assays on a droplet actuator. In one embodiment, assays of the appropriate glycosidase activity may be used to detect altered activity of a particular glycosidase, which may be an indicator of a particular lysosomal storage disease. Examples of enzyme deficiencies and LSDs include, but are not limited to, the following: a deficiency in iduronate-2-sulfae sulphatase is a diagnostic indicator of Hunter disease; a deficiency in acid β-D-glucosidase or chitotriosidase is a diagnostic indicator of Gaucher disease; a deficiency in acid sphingomyelinase or chitotriosidase is a diagnostic indicator of Niemann-Pick disease; a deficiency in α-glucosidase activity is a diagnostic indicator of Pompe disease; a deficiency in α-galactosidase activity is a diagnostic indicator of Fabry disease; a deficiency in α-L-iduronidase is a diagnostic indicator of Hurler disease; a deficiency in heparan sulfate sulfamidase is a diagnostic indicator of Sanfilippo A (MPS IIIA); a deficiency in alpha-N-acetylglucosaminidase is a diagnostic indicator of Sanfilippo B (MPS IIIB); and a deficiency in arylsulfatase A is a diagnositic indicator of metachromatic leukodystrophy. Multiple diseases and/or multiple samples can be tested simultaneously on a single droplet actuator.

The lysosomal enzyme tests are performed in aqueous droplets within an oil filled gap of the droplet actuator. Samples and assay reagents are manipulated as discrete droplets upon an electrode array (digital electrowetting). Sample droplets are blood or blood-derived samples, such as plasma, serum, tissue, cell fractions, and treated, fractionated, concentrated and/or diluted forms of the foregoing. For example, diagnosis for Pompe disease is performed on fibroblasts. Other biological fluids may be used as samples; nonlimiting examples include tears, semen, urine, saliva, amniotic liquid and cerebrospinal fluid. For example, in the testing to diagnose Fabry disease, tears may be used as the input sample droplet. Biological fluids may be treated as necessary to prepare them for being subjected to the protocols of the invention. For example, samples may be diluted or buffered, heated or cooled; pH may be adjusted; and/or blood samples may be treated with one or more anticoagulants. In some embodiments, the sample includes a reconstituted dried blood spot and/or dried plasma spot. Samples may be loaded into a reservoir associated with a droplet actuator, and may be dispensed into one or more subsamples. In some cases, the subsamples are unit-sized subsamples. The subsamples may be in contact with or surrounded with one or more filler fluids.

Assay reagents for testing for lysosomal storage disorders (e.g., LSDs) on a droplet actuator may include any one or more of the following: reaction buffer, 4-MU enzyme substrate, supplemented secondary enzyme, assay-specific inhibitor, and stop buffer (e.g., 0.2M Sodium bicarbonate pH 10.0 with 0.01% Tween® 20). Examples of 4-MU substrates include, but are not limited to, 4-Methylumbelliferyl-α-L-Iduronide-2-Sulfate (4-MU-αIdoA-2S), Hunter substrate; 4-Methylumbelliferyl α-D-Galactopyranoside (4-MU-α Gal), Fabry substrate; 4-MU-α-D-glucopyranoside (4-MU-α-Glue), Pompe substrate; 4-Methyumbelliferyl-β-D-Glucopyranoside (4-MU-β-Glue), Gaucher substrate; 4-Methylumbelliferyl-α-L-Iduronide Sodium Salt (4-MU-α-Idu), Hurler substrate; 4-Trifluoromethylumbelliferylchitroside, Gaucher and Niemann-Pick substrate; 4-Methylumbelliferyl-β-Galactose (4-MU-β-Galactose), Morquio B substrate; 4-Methylumbelliferyl-α-N-Sulpho-D-Glucosaminide (MU-αGlcNS), Sanfilippo A (MPS IIIA) substrate; 4-Methylumbelliferyl-α-D-N-Acetylglucosamine, Sanfilippo B (MPS IIIB); and 3-O-Sulfate-β-D-Galactosyl-4-Methylumbelliferyl), metachromatic leukodystrophy (MLD) substrate.

In one embodiment, the invention provides a 4-MU assay in which a droplet comprising assay reagents and a zwitterionic surfactant is dispensed and merged using droplet operations with a sample droplet in a droplet operations gap or on a droplet operations surface. The combined reaction droplet is split using droplet operations into 2 reaction droplets. One reaction droplet is combined using droplet operations with a stop buffer droplet. Fluorescence of the combined droplet is measured (t=0 h). The second reaction droplet is incubated for a predetermined time and then the reaction droplet is combined with a stop buffer droplet. End point fluorescence is measured (t=END h). In this example, a single sample droplet is dispensed and analyzed. However, any number of sample droplets may be dispensed and analyzed. The concentration of zwitterionic surfactant is preferably about in the range of 1.5 times the surfactant's critical micellar concentration (CMC). Examples of suitable zwitterionic surfactants (detergents) include n-octylphosphocholine (FOS-Choline®-8), n-nonylphosphocholine (FOS-Choline®-9), n-decylphosphocholine (FOS-Choline®-10), n-dodecylphosphocholine (FOS-Choline®-12), 3-Cyclohexyl-1-propylphosphocholine (CYCLOFOS™-3), decylphospho-N-methylethanolamine (FOS-MEA®-10), n-Decyl-N,N-dimethylglycine, n-Octyl-N,N-dimethyl-3-ammonio-1-propanesulfonate (ZWITTERGENT® 3-8), n-decyl-N,N-dimethyl-3-ammonio-1-propanesulfonate (ZWITTERGENT® 3-10), n-dodecyl-N,N-dimethyl-3-ammonio-1-propanesulfonate (ZWITTERGENT® 3-12), n-Tetradecyl-N,N-dimethyl-3-ammonio-1-propanesulfonate (ZWITTERGENT® 3-14), dimethylbenzylammonium propane sulfonate (NDSB-256), 3-[(3-cholamidopropyl)-dimethylammonio]-1-propane sulfonate (CHAPS), and 3-[(3-cholamidopropyl)-dimethylammonio]-2-hydroxy-1-propanesulfonate (CHAPSO). The droplet operations gap or surface may be coated, filled or partially filled with a filler fluid. For example, the filler fluid may be 5 cSt Silicone oil with 0.1% Triton X15.

In another embodiment, the invention provides a 4-MU assay in which a droplet comprising assay reagents and a non-ionic surfactant is dispensed and merged using droplet operations with a sample droplet in a droplet operations gap or on a droplet operations surface. The combined reaction droplet is split using droplet operations into 2 reaction droplets. One reaction droplet is combined using droplet operations with a stop buffer droplet. Fluorescence of the combined droplet is measured (t=0 h). The second reaction droplet is incubated for a predetermined time and then the reaction droplet is combined with a stop buffer droplet. End point fluorescence is measured (t=END h). In this example, a single sample droplet is dispensed and analyzed. However, any number of sample droplets may be dispensed and analyzed. The concentration of non-ionic surfactant is preferably about in the range of 1.5 times the surfactant's critical micellar concentration (CMC). Examples of suitable non-ionic surfactants (detergents) include n-hexyl-β-D-glucopyranoside, 2-cyclohexyl-1-ethyl-β-D-maltoside (CYMAL®-2), 3-cyclohexyl-1-propyl-β-D-maltoside (CYMAL®-3), octanoyl-N-methylglucamide (MEGA-8), nonanoyl-N-methylglucamide (MEGA-9), octanoyl-N-hydroxyethylglucamide (HEGA®-8), nonanoyl-N-hydroxyethylglucamide (HEGA®-9), n-hexyl-β-D-glucopyranoside, and α-[4-(1,1,3,3-tetramethylbutyl)phenyl]-δ-hydroxy-poly(oxy-1,2-ethanediyl) (ANAPOE®X-305). The droplet operations gap or surface may be coated, filled or partially filled with a filler fluid. For example, the filler fluid may be 5 cSt Silicone oil with 0.1% Triton X15.

In yet another embodiment, the invention provides a 4-MU assay in which a droplet comprising assay reagents and an ionic surfactant is dispensed and merged using droplet operations with a sample droplet in a droplet operations gap or on a droplet operations surface. The combined reaction droplet is split using droplet operations into 2 reaction droplets. One reaction droplet is combined using droplet operations with a stop buffer droplet. Fluorescence of the combined droplet is measured (t=0 h). The second reaction droplet is incubated for a predetermined time and then the reaction droplet is combined with a stop buffer droplet. End point fluorescence is measured (t=END h). In this example, a single sample droplet is dispensed and analyzed. However, any number of sample droplets may be dispensed and analyzed. The concentration of ionic surfactant is preferably about in the range of 1.5 times the surfactant's critical micellar concentration (CMC). Examples of suitable ionic surfactants (detergents) include cationic Benzyldimethyldodecylammonium bromide (BAM) and anionic 3α,7α,12α-Trihydroxy-5β-cholan-24-oic acid, monosodium salt (Sodium cholate). The droplet operations gap or surface may be coated, filled or partially filled with a filler fluid. For example, the filler fluid may be 5 cSt Silicone oil with 0.1% Triton X15.

8.3 Droplet Actuators and Hydrophobic Coatings

Figure 3:
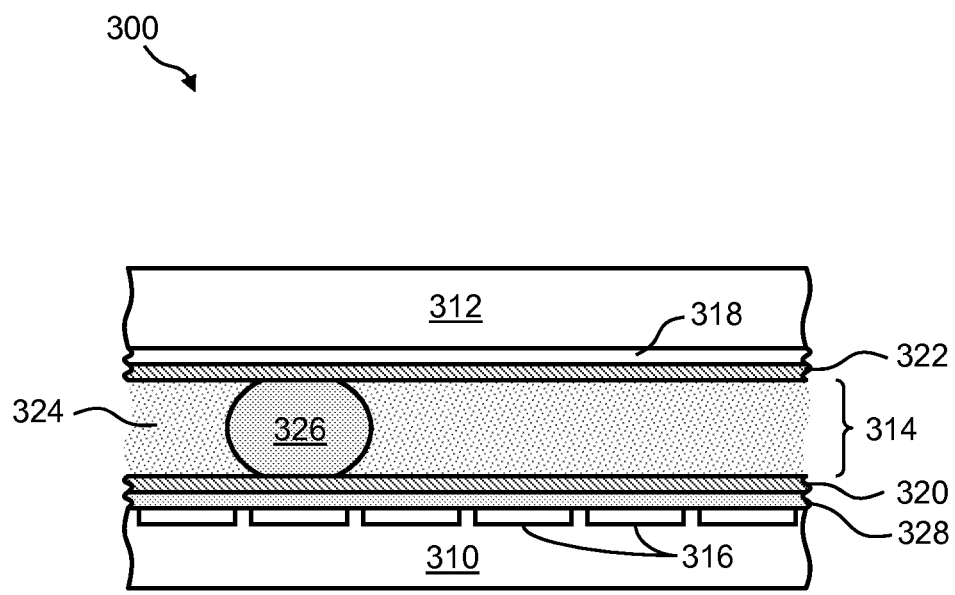
FIG. 3 illustrates a side view of a portion of an example of a droplet actuator that has hydrophobic coatings on the droplet operations surfaces thereof and the gap may be filled with perfluorinated oil.

FIG. 3 illustrates cross section of a portion of an example of a droplet actuator 300 that has hydrophobic coatings on the droplet operations surfaces. The gap in droplet actuator 300 may be filled with perfluorinated oil. Droplet actuator 300 may include a bottom substrate 310 and a top substrate 312 that are separated by a gap 314. Bottom substrate 310 may, for example, be a printed circuit board (PCB), plastic, silicon, glass, or other suitable material. Top substrate 312 may, for example, be formed of glass, injection-molded plastic, silicon, or other suitable material. Bottom substrate 310 may include an arrangement of droplet operations electrodes 316 (e.g., electrowetting electrodes). Droplet operations electrodes 316 are arranged in a manner that permits them to be used to mediate droplet operations using droplets in the droplet operations gap. Top substrate 312 may include a conductive layer 318. Conductive layer 318 is on the side of top substrate 312 that is facing gap 314. In one example, conductive layer 318 is formed of indium tin oxide (ITO), which is a material that is electrically conductive and substantially transparent to light. Droplet operations are conducted between droplet operations electrodes 316 and conductive layer 318. Droplet operations electrodes 316 of bottom substrate 310 are coated with a dielectric material 328. A hydrophobic layer 320 is provided atop dielectric material 328 of bottom substrate 310. A hydrophobic layer 322 is provided atop conductive layer 318 of top substrate 312.

In operation, gap 314 of droplet actuator 300 is filled or partially filled with a filler fluid 324. Filler fluid 324 may be a perfluorinated oil or solvent, such as perfluorinated silicone oil. One or more droplets 326 are provided in gap 314. Droplet 326 may be subjected to droplet operations the filler fluid 324. These droplet operations are mediated by droplet operations electrodes 316.

8.3.1 Water Contact Angle

Figure 4A:
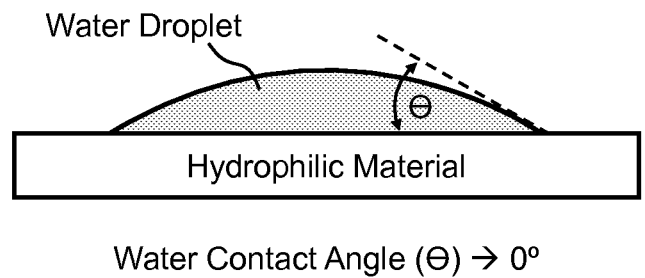
FIGS. 4A and 4B illustrate water contact angle (θ) with respect to hydrophilicity and hydrophobicity, respectively.
Figure 4B:
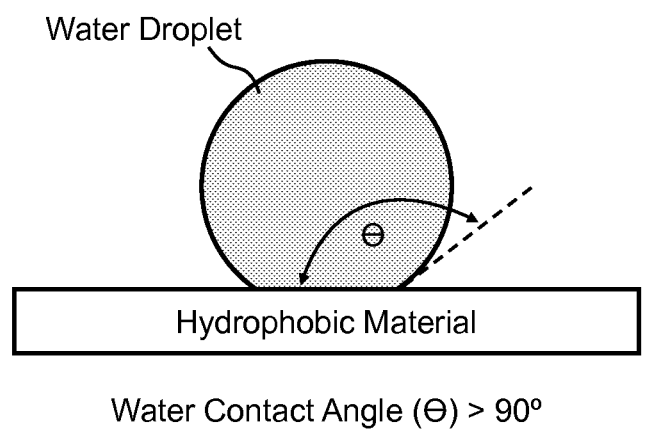

FIGS. 4A and 4B illustrate water contact angle (θ) with respect to hydrophilicity and hydrophilicity, respectively. Referring to FIG. 4A, a water droplet tends to spread on a hydrophilic surface. The evaluation of hydrophilicity is made through water contact angle (θ) measurements. Referring to FIG. 4B, hydrophobicity refers to the physical property of a material that repels a mass of water. Because a water droplet is repelled by hydrophobic material, a water droplet tends to contact only a small area of the surface and the shape of the droplet is spherical.

8.3.2 Evaluation of CYTOP® Liquid Deposition and Other PECVD Processes

Details of examples of evaluating various chemistries and various methods of depositing hydrophobic coatings are described with reference to Tables 4, 5, and 6 and FIGS. 5A through 9 below. Water contact angle (θ) and hysteresis evaluations as well as droplet operations tests were performed on M-type CYTOP® coating (an amorphous fluoropolymer) that is deposited on a substrate via a liquid deposition process. Additionally, water contact angle (θ) and hysteresis evaluations as well as droplet operations tests were performed on hydrophobic coatings deposited on a substrate via various plasma-enhanced chemical vapor deposition (PECVD) processes. PECVD is a process used to deposit thin films from a gas state (vapor) to a solid state on a substrate. For example, tests were performed using the PECVD system from Plasmatreat US LP (Elgin, Ill.). Other tests were performed using the PECVD system from Triton Systems, Inc. (Chelmsford, Mass.), which is a spray-based process. Yet other tests were performed using the PECVD system from GVD Corporation (Cambridge, Mass.), which is a chamber-based process. The M-type CYTOP® coating evaluation may be considered the standard against which the PECVD processes are evaluated. In all cases, the droplet operations performance is evaluated with respect to perfluorinated oil or solvent, such as silicone oil, in the gap of a droplet actuator.

Water contact angle (θ) and respective hysteresis values were determined for various treatments of a glass surface. For example, the surface of a glass slide (e.g., 25 mm×25 mm×1 mm thick) was treated and evaluated with respect to water contact angle (θ) and hysteresis. For each sample, a water droplet of known volume is deposited on the glass and then the water contact angle (θ) is measured using a goniometer. When liquid is added to the droplet, the volume of the droplet increases and, therefore, the water contact angle (θ) also increases. This is referred to as theta advancing (θa). Theta advancing (θa) is greater than the static water contact angle (θs), or θa>θs. By contrast, when liquid is removed from the droplet, the volume of the droplet decreases and, therefore, the water contact angle (θ) also decreases. This is referred to as theta receding (θr). Theta receding (θr) is less than the static water contact angle (θs), or θr<θs. A hysteresis value is determined by θa minus θr, or hysteresis=θa−θr.

Table 4 shows an example of evaluation results for five initial screening tests. The five tests are summarized as follows.

Test #1 is M-type CYTOP® coating liquid deposition process on glass at high temperature (i.e., 120° C.). FIGS. 3A and 3B show droplet operations tests related to Test #1.

Test #2 is hydrophobic coatings deposited on glass using the Plasmatreat PECVD process. FIG. 4 shows a droplet operations test related Test #2.

Test #3 is hydrophobic coatings deposited on glass using the Triton PECVD process. FIG. 5 shows a droplet operations test related Test #3.

Figure 6:
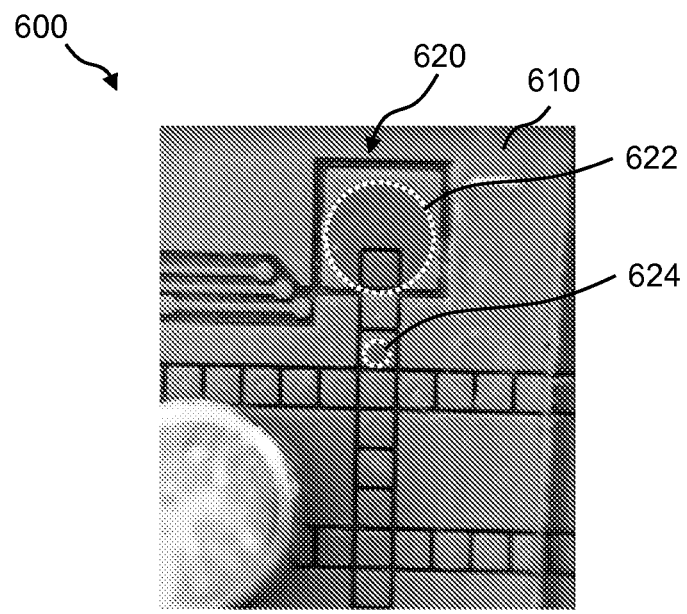
FIG. 6 shows a top down view of a portion of a droplet actuator that includes hydrophobic coatings applied using the Plasmatreat PECVD process.

Test #4 is hydrophobic coatings deposited on glass using the GVD PECVD process at room temperature. FIG. 6 shows a droplet operations test related Test #4.

Figure 7:
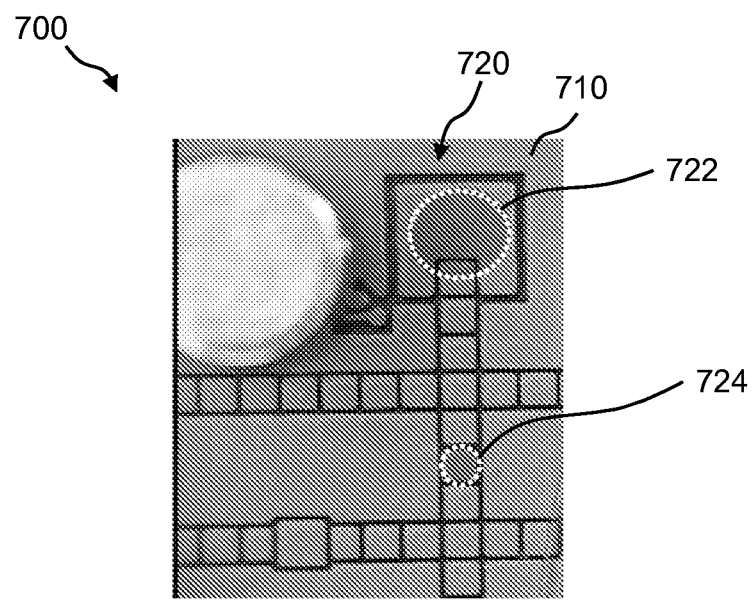
FIG. 7 shows a top down view of a portion of a droplet actuator that includes hydrophobic coatings applied using the Triton PECVD process.

Test #5 is hydrophobic coatings deposited on glass using the GVD PECVD process at high temperature (i.e., 125° C.). FIG. 7 shows a droplet operations test related Test #5.

TABLE 4

Evaluation results: Water contact angle (θ) and Hysteresis values

| Test | Process | Water Contact Angle (θ) | Hysteresis |
|---|---|---|---|
| #1 | M-type CYTOP ® coating (120° C.) | 114 | 15 |
| #2 | Plasmatreat PECVD | 85 | 12 |
| #3 | Triton PECVD | 104 | 20 |
| #4 | GVD PECVD (room temp) | 122 | 65 |
| #5 | GVD PECVD (125° C.) | 150 | 30 |

Following the aforementioned tests, droplet operations performance was tested on five droplet actuators. The five droplet actuators had bottom substrates coated with M-type CYTOP® coating per the liquid deposition process. However, the respective top substrates are unique in each test, as described with reference to FIGS. 5A through 9. This evaluation is performed to determine whether the hydrophobic coatings perform well under standard droplet operations conditions.

Figure 5A:
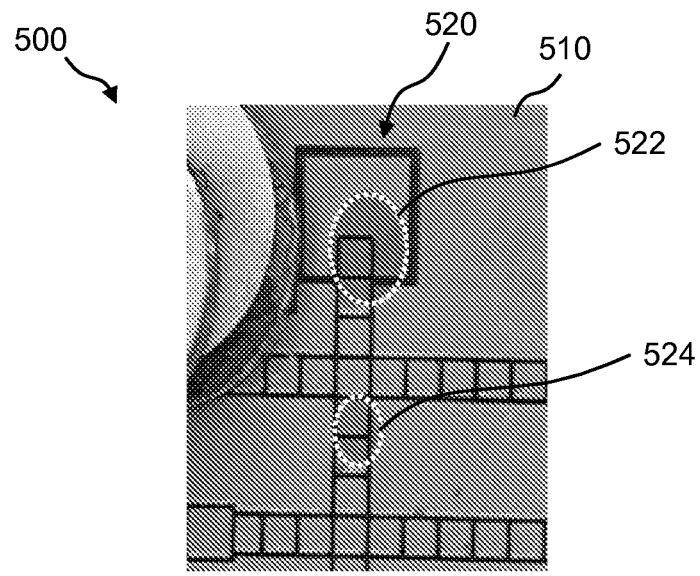
FIGS. 5A and 5B show top down views of a portion of a droplet actuator that includes M-type CYTOP® coatings applied using the liquid deposition process.
Figure 5B:
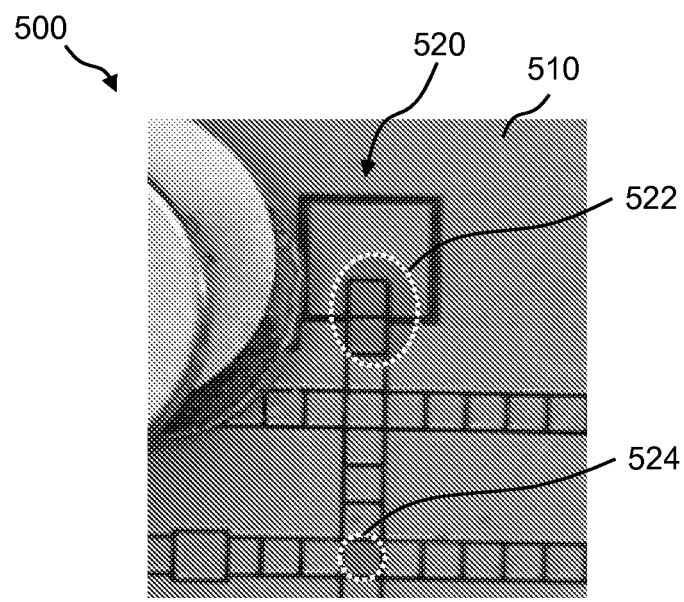

FIGS. 5A and 5B show top down views of a portion of a droplet actuator 500 that includes M-type CYTOP® coatings applied using the liquid deposition process, which substantially corresponds to the process used in Test #1 of Table 4. Droplet actuator 500 includes bottom substrate 510. An electrode arrangement 520 is patterned on bottom substrate 510. Electrode arrangement 520 may include, for example, various reservoir electrodes (of on-actuator reservoirs) and droplet operations electrodes. In the top down view of droplet actuator 500, bottom substrate 510 is visible through a substantially transparent top substrate, which is present but not visible. Bottom substrate 510 and the top substrate (not visible) are separated by a gap.

In this example, bottom substrate 510 is a PCB that is coated with M-type CYTOP® coating per the liquid deposition process. The top substrate (not visible) is formed of ITO-coated glass that is also coated with M-type CYTOP® coating per the liquid deposition process. The gap between bottom substrate 510 and the top substrate is filled with silicone oil.

In a test performed on droplet actuator 500, droplet operations are conducted atop the various electrodes to determine the droplet operations performance of M-type CYTOP® coating with respect to silicone oil. FIGS. 5A and 5B show a volume of fluid 522 at a reservoir electrode, which is the electrode of an on-actuator reservoir. A droplet 524 is dispensed from the fluid 522 at the on-actuator reservoir and transported along a line of droplet operations electrodes. FIGS. 5A and 5B show that a droplet of fluid is successfully dispensed from the on-actuator reservoir. Further, the size of the droplet is suitable for use in assay protocols and the droplet transported well.

FIG. 6 shows a top down view of a portion of a droplet actuator 600 that includes hydrophobic coatings applied using the Plasmatreat PECVD process, which substantially corresponds to the process used in Test #2 of Table 4. Droplet actuator 600 includes bottom substrate 610. An electrode arrangement 620 is patterned on bottom substrate 610. Electrode arrangement 620 may include, for example, various reservoir electrodes (of on-actuator reservoirs) and droplet operations electrodes. In the top down view of droplet actuator 600, bottom substrate 610 is visible through a substantially transparent top substrate, which is present but not visible. Bottom substrate 610 and the top substrate (not visible) are separated by a gap.

In this example, bottom substrate 610 is a PCB that is coated with M-type CYTOP® coating per the liquid deposition process. However, the top substrate (not visible) is formed of ITO-coated glass that is coated with hydrophobic material per the Plasmatreat PECVD process. The gap between bottom substrate 610 and the top substrate is filled with silicone oil.

In a test performed on droplet actuator 600, droplet operations are conducted atop the various electrodes to determine the droplet operations performance of the hydrophobic material deposited via the Plasmatreat PECVD process with respect to silicone oil. FIG. 6 shows a volume of fluid 622 at a reservoir electrode, which is the electrode of an on-actuator reservoir. A droplet 624 is dispensed from the fluid 622 at the on-actuator reservoir and transported along a line of droplet operations electrodes. FIG. 6 shows that a droplet of fluid is successfully dispensed from the on-actuator reservoir. However, the size of the droplet is not suitable for use in assay protocols and the droplet did not transport well.

FIG. 7 shows a top down view of a portion of a droplet actuator 700 that includes hydrophobic coatings applied using the Triton PECVD process, which substantially corresponds to the process used in Test #3 of Table 4. Droplet actuator 700 includes bottom substrate 710. An electrode arrangement 720 is patterned on bottom substrate 710. Electrode arrangement 720 may include, for example, various reservoir electrodes (of on-actuator reservoirs) and droplet operations electrodes. In the top down view of droplet actuator 700, bottom substrate 710 is visible through a substantially transparent top substrate, which is present but not visible. Bottom substrate 710 and the top substrate (not visible) are separated by a gap.

In this example, bottom substrate 710 is a PCB that is coated with M-type CYTOP® coating per the liquid deposition process. However, the top substrate (not visible) is formed of ITO-coated glass that is also coated with hydrophobic material per the Triton PECVD process. The gap between bottom substrate 710 and the top substrate is filled with silicone oil.

In a test performed on droplet actuator 700, droplet operations are conducted atop the various electrodes to determine the droplet operations performance of the hydrophobic material deposited via the Triton PECVD process with respect to silicone oil. FIG. 7 shows a volume of fluid 722 at a reservoir electrode, which is the electrode of an on-actuator reservoir. A droplet 724 is dispensed from the fluid 722 at the on-actuator reservoir and transported along a line of droplet operations electrodes. FIG. 7 shows that a droplet of fluid is successfully dispensed from the on-actuator reservoir. Further, the size of the droplet is suitable for use in assay protocols and the droplet transported well.

Figure 8:
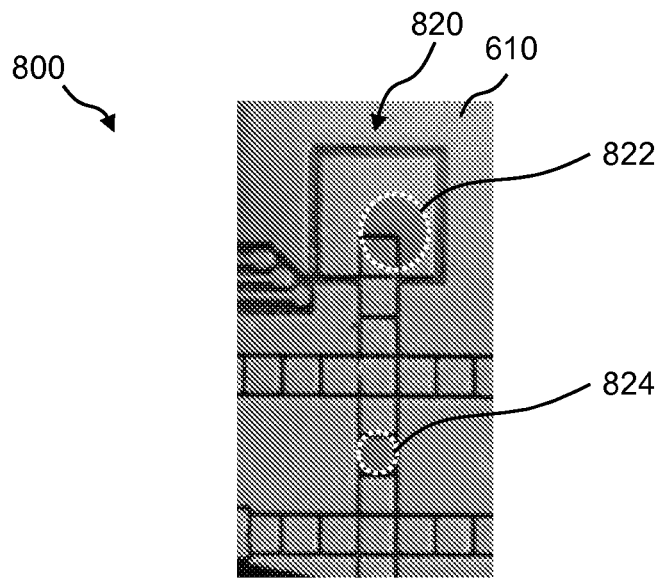
FIG. 8 shows a top down view of a portion of a droplet actuator that includes hydrophobic coatings applied using the GVD PECVD process at room temperature.

FIG. 8 shows a top down view of a portion of a droplet actuator 800 that includes hydrophobic coatings applied using the GVD PECVD process at room temperature, which substantially corresponds to the process used in Test #4 of Table 4. Droplet actuator 800 includes bottom substrate 810. An electrode arrangement 820 is patterned on bottom substrate 810. Electrode arrangement 820 may include, for example, various reservoir electrodes (of on-actuator reservoirs) and droplet operations electrodes. In the top down view of droplet actuator 800, bottom substrate 810 is visible through a substantially transparent top substrate, which is present but not visible. Bottom substrate 810 and the top substrate (not visible) are separated by a gap.

In this example, bottom substrate 810 is a PCB that is coated with M-type CYTOP® coating per the liquid deposition process. However, the top substrate (not visible) is formed of ITO-coated glass that is also coated with hydrophobic material per the GVD PECVD process at room temperature. The gap between bottom substrate 810 and the top substrate is filled with silicone oil.

In a test performed on droplet actuator 800, droplet operations are conducted atop the various electrodes to determine the droplet operations performance of the hydrophobic material deposited via the GVD PECVD process at room temperature with respect to silicone oil. FIG. 8 shows a volume of fluid 822 at a reservoir electrode, which is the electrode of an on-actuator reservoir. A droplet 824 is dispensed from the fluid 822 at the on-actuator reservoir and transported along a line of droplet operations electrodes. FIG. 8 shows that a droplet of fluid is successfully dispensed from the on-actuator reservoir. Further, the size of the droplet is suitable for use in assay protocols and the droplet transported well.

Figure 9:
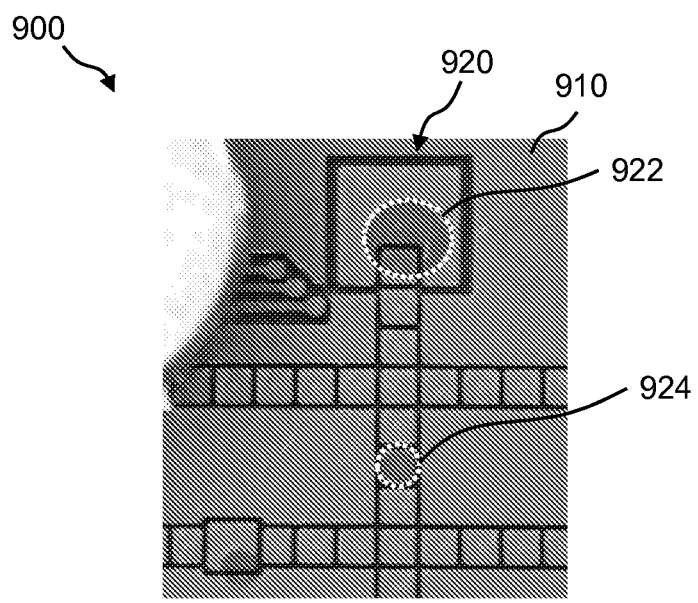
FIG. 9 shows a top down view of a portion of a droplet actuator that includes hydrophobic coatings applied using the GVD PECVD process at high temperature.

FIG. 9 shows a top down view of a portion of a droplet actuator 900 that includes hydrophobic coatings applied using the GVD PECVD process at high temperature (e.g., about 125° C.), which substantially corresponds to the process used in Test #5 of Table 4. Droplet actuator 900 includes bottom substrate 910. An electrode arrangement 920 is patterned on bottom substrate 910. Electrode arrangement 920 may include, for example, various reservoir electrodes (of on-actuator reservoirs) and droplet operations electrodes. In the top down view of droplet actuator 900, bottom substrate 910 is visible through a substantially transparent top substrate, which is present but not visible. Bottom substrate 910 and the top substrate (not visible) are separated by a gap.

In this example, bottom substrate 910 is a PCB that is coated with M-type CYTOP® coating per the liquid deposition process. However, the top substrate (not visible) is formed of ITO-coated glass that is also coated with hydrophobic material per the GVD PECVD process at high temperature. The gap between bottom substrate 910 and the top substrate is filled with silicone oil.

In a test performed on droplet actuator 900, droplet operations are conducted atop the various electrodes to determine the droplet operations performance of the hydrophobic material deposited via the GVD PECVD process at high temperature with respect to silicone oil. FIG. 9 shows a volume of fluid 922 at a reservoir electrode, which is the electrode of an on-actuator reservoir. A droplet 924 is dispensed from the fluid 922 at the on-actuator reservoir and transported along a line of droplet operations electrodes. FIG. 9 shows that a droplet of fluid is successfully dispensed from the on-actuator reservoir. Further, the size of the droplet is suitable for use in assay protocols and the droplet transported well.

Referring again to Table 4 and FIGS. 5A through 9, the samples having a water contact angle (θ) greater than about 100 correlate to the samples having the most suitable droplet operations performance. For example, the samples of Tests #1, #3, #4, and #5 have water contact angles (θ) greater than about 100, while the corresponding droplet actuators 300, 500, 600, and 700, respectively, demonstrated suitable droplet operations performance By contrast, the sample of Test #2 has a water contact angle (θ) of about 85 and the corresponding droplet actuator 400 did not demonstrate suitable droplet operations performance. Therefore, in certain circumstances, the Plasmatreat PECVD process may be a less desirable process for depositing hydrophobic material on a droplet actuator.

Additionally, while the hydrophobic material deposited via the GVD PECVD process at room temperature and at high temperature provides a good hydrophobic surface, the hydrophobic surface is brittle. Therefore, in certain circumstances, the GVD PECVD process may not be a preferred process for depositing hydrophobic material on a droplet actuator. As a result, the M-type CYTOP® coating liquid deposition process and the Triton PECVD process may be a less desirable processes for depositing hydrophobic material on a droplet actuator.

8.3.3 Evaluation of Solubility

With respect to the M-type CYTOP® coating liquid deposition process, currently the M-type CYTOP® coating is cured at about 93° C. for 1 hour. Tests were performed to evaluate the water contact angle (θ) and hysteresis when M-type CYTOP® coating samples are cured at up to about 200° C., before and after exposure to Galden® HT170 fluid (a perfluoropolyether) for about 2 hours. The Galden® HT170 fluid is an example of a specific brand of perfluorinated solvent that is available from Solvay Solexis (West Deptford, N.J.). M-type CYTOP® coating samples were prepared and cured at various temperatures in order to evaluate the chemical stability to Galden® HT170 fluid. The preference is that the high temperature cure results in little or no change in water contact angle (θ) and hysteresis. Table 5 shows chemical stability results of samples treated with M-type CYTOP® coating process vs. GVD PECVD process vs. Triton PECVD process before and after exposure to Galden® HT170 fluid.

TABLE 5

Chemical stability results of samples treated with M-type CYTOP ® coating process vs. GVD process vs. Triton process before and after exposure to Galden ® HT170 fluid

|  | M-type CYTOP ® (LT) | M-type CYTOP ® (MT) | M-type CYTOP ® (HT) | M-type CYTOP ® (XHT) | GVD (HT) | Triton |
|---|---|---|---|---|---|---|
| Cure Temp (° C.)/Time (minutes) | 93/60 | 120/60 | 80/30 + 160/30 | 80/30 + 200/60 | 125° C. | N/A |
| Thickness (nanometers) | 200 | 200 | 400 | 200 | 250 | 200 |
| *Water contact angle (θ) before exposure to HT170 @ 60° C. for 2 hrs | 113/1 | 113/1 | 112/1 | 113/2 | 146/3 | 104/1 |
| *Hysteresis before exposure to HT170 @ 60° C. for 2 hrs | 12/1 | 12/1 | 12/1 | 13/1 | 35/2 | 22/2 |
| *Water contact angle (θ) after exposure to HT170 @ 60° C. for 2 hrs | 107/4 | 113/1 | 112/1 | 110/5 | 138/3 | 104/1 |
| *Hysteresis after exposure to HT170 @ 60° C. for 2 hrs | 12/1 | 18/2 | 15/3 | 15/2 | 37/6 | 23/0 |

*xx/x means value/standard deviation

In each test, a droplet was deposited on the glass slide and the water contact angle (θ) and hysteresis were measured. In the process of testing the samples before and after exposure to Galden® HT170 fluid, the samples were washed with isopropyl alcohol between runs.

Referring to Table 5, the test results show a slight decrease in water contact angle (θ) after exposure to Galden® HT170 fluid. The HT170 did not affect the droplet operations performance for M-type CYTOP® coating cured at low temperature (93° C.), mid-temperature (120° C.), and high temperature (160° C.).

Referring now to Table 6, tests were performed before and after exposure to Novec™ 7500 engineered fluid (available from 3M of St. Paul, Minn.) for about 2 hours. M-type CYTOP® coating samples were prepared and cured at various temperatures in order to evaluate the chemical stability to the Novec™ 7500 fluid.

TABLE 6

Chemical stability results of samples treated with M-type CYTOP ® coating process before and after exposure to Novec ™ 7500 fluid

|  | M-type CYTOP ®(LT) | M-type CYTOP ®(MT) | M-type CYTOP ®(HT) | M-type CYTOP ®(XHT) |
| --- | --- | --- | --- | --- |
| Cure Temp (° C.)/ Time (minutes) | 93/60 | 120/60 | 80/30 + 160/30 | 80/30 + 200/60 |
| Thickness (nanometers) | 200 | 200 | 400 | 200 |
| *Water contact angle (θ) before exposure to Novec ™ 7500 @ 60° C. for 2 hrs | 113/1 | 113/1 | 112/1 | 113/2 |
| *Hysteresis before exposure to Novec ™ 7500 @ 60° C. for 2 hrs | 12/1 | 12/1 | 12/1 | 13/1 |
| *Water contact angle (θ) after exposure to Novec ™ 7500 @ 60° C. for 2 hrs | 102/1 | 102/3 | 109/3 | 111/2 |
| *Hysteresis after exposure to Novec ™ 7500 @ 60° C. for 2 hrs | 41/6 | 37/7 | 15/4 | 13/4 |

*xx/x means value/standard deviation

Referring again to Tables 4 and 5, with respect to the M-type CYTOP® coating liquid deposition process, the extra-high temperature process (i.e., 160° C. to 200° C.) for about 1 hour may be the preferred process. Optionally, the high temperature cure step and/or the extra-high temperature cure step may be preceded by a prebake step at 80° C. for about 30 minutes.

8.4 Systems

Figure 10:
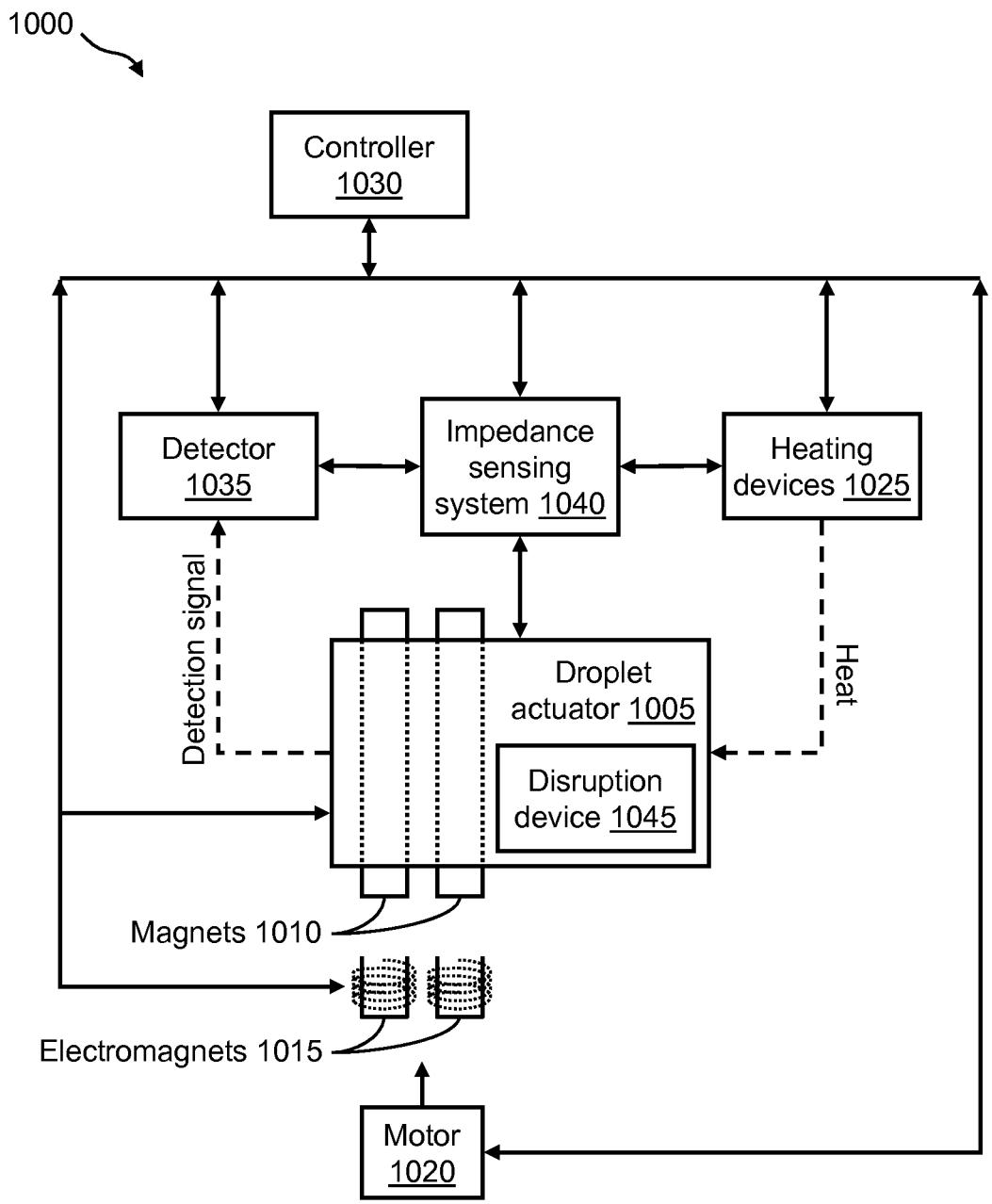
FIG. 10 illustrates a functional block diagram of an example of a microfluidics system that includes a droplet actuator.

FIG. 10 illustrates a functional block diagram of an example of a microfluidics system 1000 that includes a droplet actuator 1005. Digital microfluidic technology conducts droplet operations on discrete droplets in a droplet actuator, such as droplet actuator 1005, by electrical control of their surface tension (electrowetting). The droplets may be sandwiched between two substrates of droplet actuator 1005, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (i.e., the gap between bottom and top substrates) may be filled with an immiscible inert fluid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 1005 may be designed to fit onto an instrument deck (not shown) of microfluidics system 1000. The instrument deck may hold droplet actuator 1005 and house other droplet actuator features, such as, but not limited to, one or more magnets and one or more heating devices. For example, the instrument deck may house one or more magnets 1010, which may be permanent magnets. Optionally, the instrument deck may house one or more electromagnets 1015. Magnets 1010 and/or electromagnets 1015 are positioned in relation to droplet actuator 1005 for immobilization of magnetically responsive beads. Optionally, the positions of magnets 1010 and/or electromagnets 1015 may be controlled by a motor 1020. Additionally, the instrument deck may house one or more heating devices 1025 for controlling the temperature within, for example, certain reaction and/or washing zones of droplet actuator 1005. In one example, heating devices 1025 may be heater bars that are positioned in relation to droplet actuator 1005 for providing thermal control thereof.

A controller 1030 of microfluidics system 1000 is electrically coupled to various hardware components of the invention, such as droplet actuator 1005, electromagnets 1015, motor 1020, and heating devices 1025, as well as to a detector 1035, an impedance sensing system 1040, and any other input and/or output devices (not shown). Controller 1030 controls the overall operation of microfluidics system 1000. Controller 1030 may, for example, be a general purpose computer, special purpose computer, personal computer, or other programmable data processing apparatus. Controller 1030 serves to provide processing capabilities, such as storing, interpreting, and/or executing software instructions, as well as controlling the overall operation of the system. Controller 1030 may be configured and programmed to control data and/or power aspects of these devices. For example, in one aspect, with respect to droplet actuator 1005, controller 1030 controls droplet manipulation by activating/deactivating electrodes.

In one example, detector 1035 may be an imaging system that is positioned in relation to droplet actuator 1005. In one example, the imaging system may include one or more light-emitting diodes (LEDs) (i.e., an illumination source) and a digital image capture device, such as a charge-coupled device (CCD) camera.

Impedance sensing system 1040 may be any circuitry for detecting impedance at a specific electrode of droplet actuator 1005. In one example, impedance sensing system 1040 may be an impedance spectrometer. Impedance sensing system 1040 may be used to monitor the capacitive loading of any electrode, such as any droplet operations electrode, with or without a droplet thereon. For examples of suitable capacitance detection techniques, see Sturmer et al., International Patent Publication No. WO/2008/101194, entitled "Capacitance Detection in a Droplet Actuator," published on Aug. 21, 2008; and Kale et al., International Patent Publication No. WO/2002/080822, entitled "System and Method for Dispensing Liquids," published on Oct. 17, 2002; the entire disclosures of which are incorporated herein by reference.

Droplet actuator 1005 may include disruption device 1045. Disruption device 1045 may include any device that promotes disruption (lysis) of materials, such as tissues, cells and spores in a droplet actuator. Disruption device 1045 may, for example, be a sonication mechanism, a heating mechanism, a mechanical shearing mechanism, a bead beating mechanism, physical features incorporated into the droplet actuator 1005, an electric field generating mechanism, a thermal cycling mechanism, and any combinations thereof. Disruption device 1045 may be controlled by controller 1030.

It will be appreciated that various aspects of the invention may be embodied as a method, system, computer readable medium, and/or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the invention may be written in an object oriented programming language such as Java, Smalltalk, C++ or the like. However, the program code for carrying out operations of the invention may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The invention may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The invention may be applied to any wireless/wireline communications network, regardless of physical componentry, physical configuration, or communications standard(s).

Certain aspects of invention are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the invention.

9 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

I claim:

1. A method of conducting an assay, the method comprising:
   (a) incubating a droplet in oil, the droplet comprising an umbelliferone substrate, a sample potentially comprising an enzyme which cleaves the umbelliferone substrate, and a zwitterionic surfactant; and
   (b) detecting a signal emitted from the droplet.

2. The method of claim 1 wherein the droplet further comprises a cyclodextrin compound.

3. The method of claim 2 wherein the cyclodextrin compound is selected from the group consisting of α-cyclodextrins, β-cyclodextrins, and γ-cyclodextrins, and analogs and derivatives of the foregoing.

4. The method of claim 2 wherein the umbilliferone substrate is selected from the group consisting of alkylumbelliferyl-α-L-iduronides, 4-methylumbelliferyl-α-L-iduronide, 4-methylumbelliferyl-α-L-iduronide-2-sulfate, 4-methylumbelliferyl-α-L-idopyranosiduronic acid, 4-methylumbelliferyl-α-L-fucoside, 4-methylumbelliferyl-α-L-mannoside, 4-methylumbelliferyl-β-D-mannoside, 4-methylumbelliferyl-β-D-N-acetylglucosaminide, 4-methylumbelliferyl-β-D-N-acetylglucosaminide sulfate, alkylumbelliferyl-β-D-glycosides, methylumbelliferyl-β-D-glycosides, 4-methylumbelliferyl-α-D-galactoside, 4-methylumbelliferyl-β-D-galactoside, 4-methylumbelliferyl-β-D-glucouronic acid, phenolphthalein-β-D-glucuronic acid, ethylumbelliferyl-β-D-glycosides, multifluoroethylumbelliferyl-β-D-glycosides, pentafluoroethylumbelliferyl-β-D-glycosides, pentafluoroethylumbelliferyl-β-D-glucoside, umbelliferylchiotriosides, 4-alkyumbelliferylchiotrioside, 4-methylumbelliferyl-chiotrioside, 4-methylumbelliferyl-β-galactose, 4-alkyumbeliferrone phosphates, 4-methylumbeliferrone phosphate, 6-alkanoylamido-4-methylumbelliferones, substrates comprising a 4-methyllumbelliferyl group, 6-hexadecanoylamido-4-methylumbelliferone, 4-methyllumbelliferyl-β-D-glucosaminide, 4-methylumbelliferyl-α-neuraminic acid, 4-methylumbelliferyl-α-D-N-acetylgalactosaminide, and their functional analogs and derivatives.

5. The method of claim 1, wherein the steps are performed within droplets controlled by a droplet actuator.

6. The method of claim 5, wherein the droplet actuator controls the steps using electrode mediated droplet operations.

7. The method of claim 5, wherein the droplet actuator controls the steps using electrowetting mediated droplet operations.

8. The method of claim 5, wherein the droplet actuator controls the steps using dielectrophoresis mediated droplet operations.

9. A method of conducting a droplet-based enzyme assay, the method comprising:
   (a) providing an immiscible fluid comprising:
      (i) a sample droplet comprising an enzyme of interest; and
      (ii) one or more reagent droplets comprising:
         (1) a substrate which is potentially modified in the presence of the enzyme yielding one or more signal-producing products;
         (2) a zwitterionic surfactant; and
         (3) optionally, other reagents sufficient to produce activity of the target enzyme;
   (b) combining the sample droplet and the one or more reagent droplets in the immiscible fluid to yield a reaction droplet effecting an enzyme reaction in the immiscible fluid; and
   (c) measuring any signal produced by the one or more signal producing products.

10. The method of claim 1, wherein the zwitterionic surfactant is selected form the group consisting of n-Octylphosphocholine, n-Nonylphosphocholine, n-decylphosphocholine, n-dodecylphosphocholine, 3-cyclohexyl-1-propylphosphocholine, decylphospho-N-methylethanolamine, n-decyl-N,N-dimethylglycine, n-octyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, dimethylbenzylammonium propane sulfonate, 3-[(3-Cholamidopropyl)-dimethylammonio]-1-propane sulfonate, and 3-[(3-cholamidopropyl)-dimethylammonio]-2-hydroxy-1-propanesulfonate.

11. The method of claim 1, wherein the substrate comprises a glycoside substrate.

12. The method of claim 1, wherein the substrate releases a fluorophore upon contact with the enzyme.

13. The method of claim 12 wherein two or more assays are conducted simultaneously using different fluorophores for each enzyme tested.

14. The method of claim 12 wherein the fluorophore comprises 4-methylumbelliferyl.

15. The method of claim 1, wherein the substrate comprises a glycoside substrate which releases a fluorophore upon contact with the enzyme.

16. The method of claim 1, wherein the substrate comprises a glycoside substrate comprising glucose, galactose, fucose, mannose, sialic acid, hexose, hexosamine and/or N-acetylated hexosamine.

17. The method of claim 16 wherein the substrate comprises a 4-methylumbelliferyl glycoside.

18. The method of claim 1, further comprising reducing or eliminating reaction contaminants associated with the substrate.

19. The method of claim 18 wherein the reducing or eliminating reaction contaminants comprises photobleaching the substrate.

20. The method of claim 19 wherein the photobleaching is effected prior to providing the droplet comprising the substrate on the droplet actuator.

21. The method of claim 19 wherein the photobleaching is effected after providing the droplet comprising the substrate on the droplet actuator.

22. The method of claim 1, wherein the substrate comprises a 4-methylumbelliferyl glycoside substrate.

23. The method of claim 22 further comprising photobleaching the substrate.

24. The method of claim 9, wherein the immiscible fluid comprises a filler fluid.

25. The method of claim 9, wherein the immiscible fluid comprises a silicone oil.

26. The method of claim 24 wherein the filler fluid comprises a surfactant.

27. The method of claim 26 wherein the surfactant comprises nonionic low hydrophile-lipophile balanced (HLB) surfactant.

28. The method of claim 27 wherein the HLB is less than about 10.

29. The method of claim 27 wherein the HLB is less than about 5.

30. The method of claim 27 wherein the surfactant is selected from the group consisting of

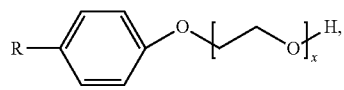

wherein R is octyl (C8) and X is 1.5 (avg);

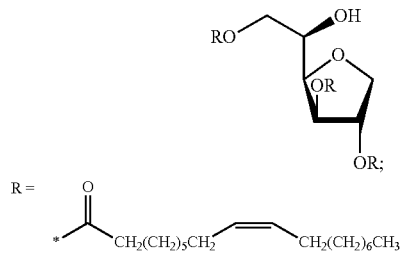

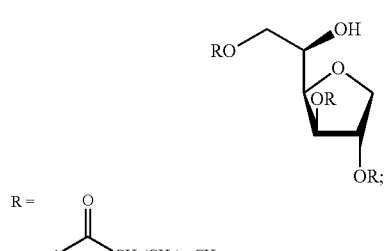

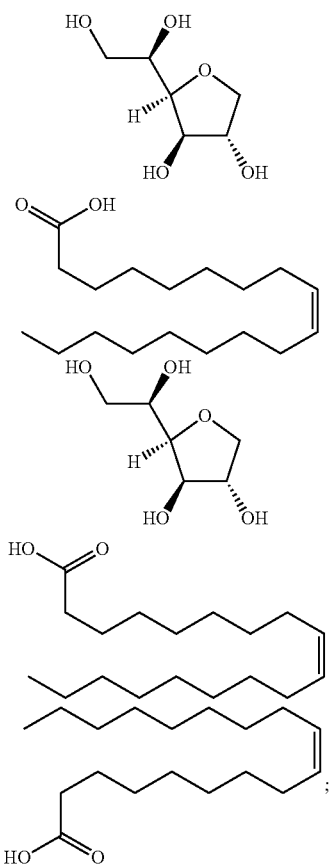

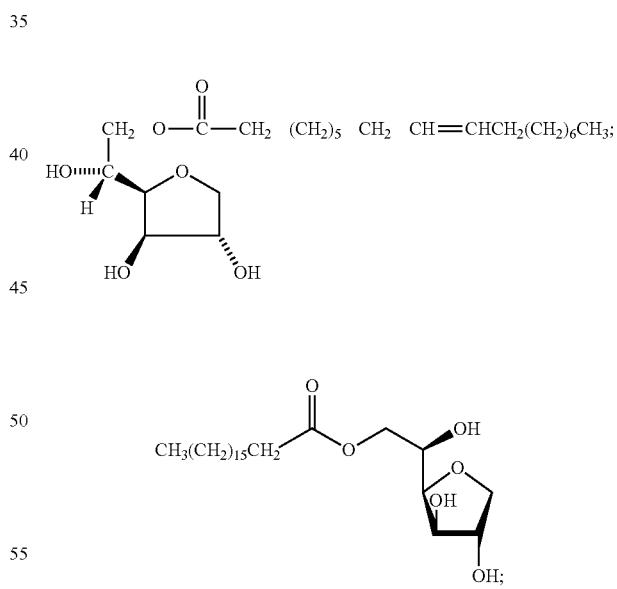

and fluorinated surfactants.

31. The method of claim 9, wherein:
(a) the sample droplet comprises a reconstituted blood sample;
(b) the blood sample is reconstituted using a single universal reconstitution solution;
(c) the blood sample is divided to yield two or more reaction droplets; and
(d) two or more of the reaction droplets are each combined with one or more sets of one or more reagent droplets, each such set comprising reagents selected for establishing reaction conditions for a different enzyme assay.

32. The method of claim 31 wherein the universal reconstitution solution comprises a saline solution.

33. The method of claim 31 wherein the universal reconstitution solution comprises water.

34. The method of claim 9, wherein the enzyme assay is selected to provide diagnostic information about an enzyme deficiency.

35. The method of claim 34 wherein the enzyme deficiency is selected from lysosomal storage diseases.

36. The method of claim 34 wherein the enzyme deficiency is selected from the group consisting of Pompe, Niemann-Pick, Fabry, Krabbe, and Gaucher.

37. The method of claim 34 further comprising providing therapeutic treatment to a subject based on the diagnostic information.

38. The method of claim 9, wherein the sample droplet comprising an enzyme of interest comprises cultured cells and/or supernatant from a cell culture.

39. The method of claim 9, wherein the substrate is selected from the group consisting of 4-methylumbelliferyl-α-L-iduronide, 4-methylumbelliferyl-β-D-galactoside, 4-methylumbelliferyl-β-D-glucuronic acid, 4-methylumbelliferyl-α-L-fucoside, 4-methylumbelliferyl-α-mannoside, 4-methylumbelliferyl-β-D-mannoside, 4-nitrocathecol sulfate, 4-methylumbelliferyl-β-D-N-acetylglucosaminide, 4-methylumbelliferyl-β-D-N-acetylglucosaminide sulfate, 4-methylumbelliferyl-β-D-glucosaminide, 4-methylumbelliferyl-α-D-galactoside, 4-methylumbelliferyl-α-D-neuraminic acid, 4-methylumbelliferyl-α-D-N-acetylgalactosaminide, phenolphthalein β-D-glucuronic acid, and mixtures and derivatives thereof.

40. The method of claim 9, wherein the substrate comprises a fluorophoric moiety.

41. The method of claim 40 wherein the fluorophoric moiety comprises 4-methyllumbelliferyl.

42. The method of claim 9, wherein the substrate comprises a chromophoric moiety.

43. The method of claim 42 wherein the chromophoric moiety comprises 4-nitrocathecol or phenolphthalein.

44. The method of claim 9, wherein the substrate comprises a radioactive moiety.

45. The method of claim 44 wherein the radioactive moiety comprises $^{14}C$ sphingomyelin or $^{3}H$ galactosylceramide.

46. The method of claim 9, comprising incubating the reaction droplet for a period of less than about 12 hours.

* * * * *